United States Patent
Honkura et al.

[11] Patent Number: 5,931,676
[45] Date of Patent: Aug. 3, 1999

[54] DENTAL ATTACHMENT

[75] Inventors: Yoshinobu Honkura; Takashi Yokoyama; Hideki Fujii; Yoshinobu Tanaka, all of Tokai, Japan

[73] Assignee: Aichi Steel Works, Ltd., Tokai, Japan

[21] Appl. No.: 08/702,491

[22] PCT Filed: Dec. 26, 1995

[86] PCT No.: PCT/JP95/02685

§ 371 Date: Dec. 12, 1997

§ 102(e) Date: Dec. 12, 1997

[87] PCT Pub. No.: WO96/19951

PCT Pub. Date: Jul. 4, 1996

[30] Foreign Application Priority Data

Dec. 27, 1994 [WO] WIPO .................. PCT/JP94/02228

[51] Int. Cl.⁶ ................................................ A61C 13/235
[52] U.S. Cl. ............................................................ 433/189
[58] Field of Search ........................... 433/189; 335/304, 335/306, 302

[56] References Cited

U.S. PATENT DOCUMENTS

| | | | |
|---|---|---|---|
| 5,425,763 | 6/1995 | Stemmann | 433/189 |
| 5,678,998 | 10/1997 | Honkura et al. | 433/189 |
| 5,788,493 | 8/1998 | Tanaka et al. | 433/189 |

FOREIGN PATENT DOCUMENTS

| | | |
|---|---|---|
| 57-164054 | 10/1982 | Japan . |
| 62-211061 | 9/1987 | Japan . |
| 63-281645 | 11/1988 | Japan . |
| 1-303145 | 12/1989 | Japan . |
| 2-295557 | 12/1990 | Japan . |
| 2-295558 | 12/1990 | Japan . |
| 5-285160 | 11/1993 | Japan . |
| 6-78938 | 3/1994 | Japan . |
| 6-78939 | 3/1994 | Japan . |

*Primary Examiner*—Nicholas D. Lucchesi
*Attorney, Agent, or Firm*—Jacobson, Price, Holman & Stern, PLLC

[57] ABSTRACT

A dental magnetic attachment, which is embedded in the denture base so as to face a soft magnetic keeper 103 and attract the keeper by magnetic force, comprising at least three yokes which are plates and made of soft magnetic material, and at least two pieces of magnet which have the magnetization direction parallel to the thickness. In the example the attachment comprises a central yoke 10, the magnet 1, the magnet 2, the outer yoke 11, and the outer yoke 12. The invention is characterized by a magnet arrangement in which like poles of the magnet 1 and the magnet 2 faces each other. Because of it mutually independent two magnetic circuits are formed and they offer strong attractive force which is two times larger than that of existing ones in a compact volume required for dental attachment. Furthermore, corrosion resistance and wear resistance are improved by covering the attracting face of the magnet 1, 2 with spacers made of non-magnetic material and covering the whole attachment with the cap made of non-magnetic material except the attracting face of the attachment.

36 Claims, 15 Drawing Sheets

Fig. 9
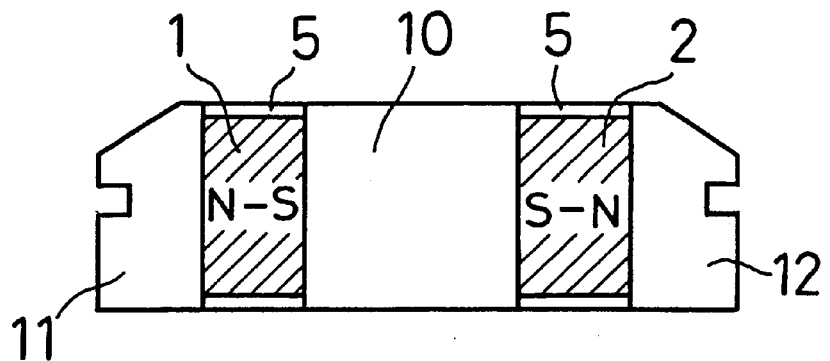
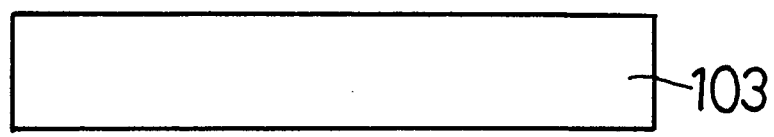
Fig. 10
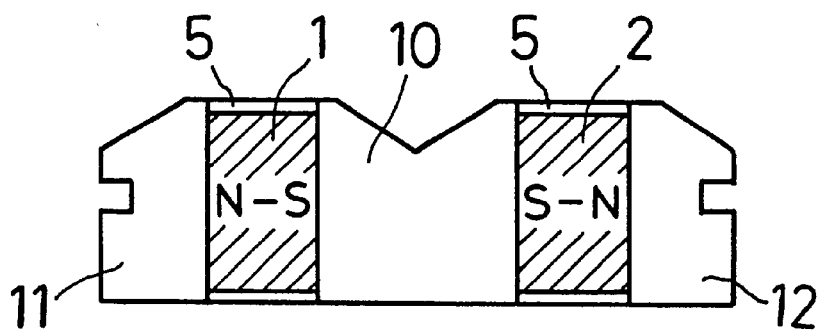
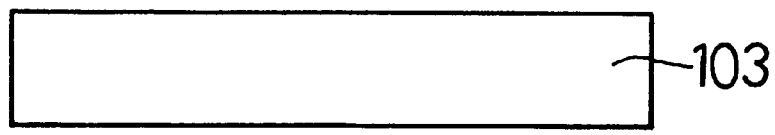

Fig. 21
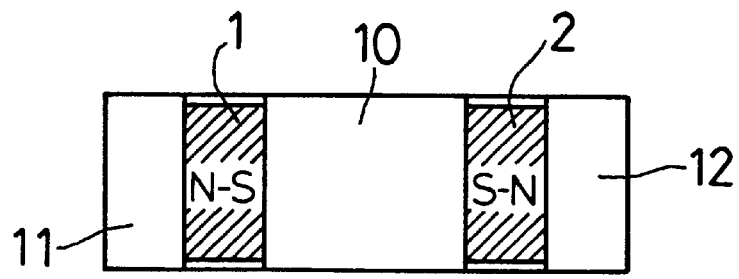
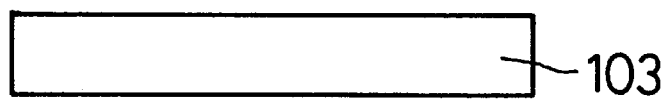
Fig. 22
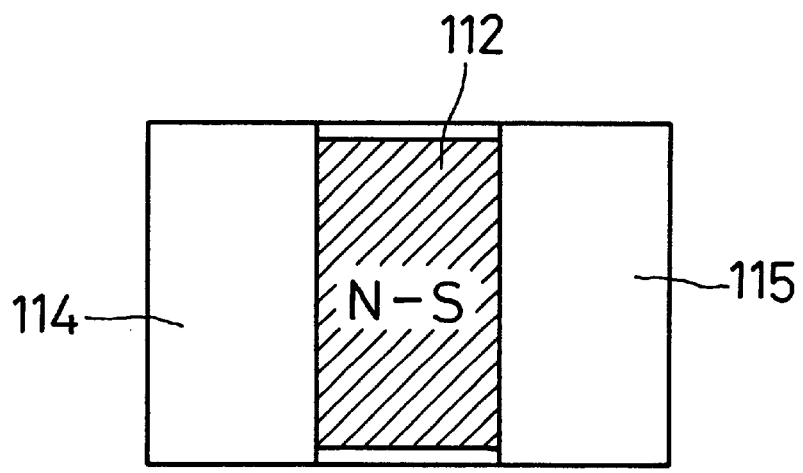

DENTAL ATTACHMENT

TECHNICAL FIELD

This invention relates to dental attachments which utilize magnetic attractive force to retain a denture on tooth roots, specifically to the ones which have thin disk shape with smaller cross section than that of tooth root.

BACKGROUND ART

As shown in FIG. 23, an existing method to attach a denture on the gingiva by a dental magnetic attachment is as follows. Root cap 102 is set on the tooth root 101 in the gingiva to form an abutment tooth for the denture 110. A keeper 103 made of corrosion-resisting soft magnetic alloy is embedded in the center of top surface of root cap 102. A dental attachment 111 is embedded in the center of bottom face of the denture so as to face the keeper 103. The attachment 111 attracts the keeper 103 magnetically, thus the denture 110 is fixed on the root surface 102.

Japanese patent application Laid-Open (Kokai) No. 1-303145, 2-295557, 2-295558 disclose a dental attachment 111 of which exploded view is shown in FIG. 24, sectional view in FIG. 25. This existing attachment consists of a block of magnet 112, a spacer 113 made of corrosion resisting non-magnetic alloy to cover one face of the magnet, a pair of yokes 114, 115 that made of corrosion resisting soft magnetic alloy to sandwich the magnet 112 and the spacer 113 in between, and a cap 116 made of corrosion resisting non-magnetic alloy to cover whole other parts. This dental attachment has a magnet 112 with the N-S direction parallel to the keeper 113. A magnetic circuit is formed in which the magnetic flux generated at the magnet 112, passes through the yoke 114, keeper 103, then the other yoke 105, finally returns to the magnet 112. This closed magnetic circuit gives relatively strong attractive force.

Japanese patent application Laid-Open (Kokai) No. 57-164054 disclose a dental attachment 121 of which magnet arrangement is shown in FIG. 26. The attachment in the denture is shown in FIG. 27. This dental attachment consists of plurality of pairs of permanent magnet 122 and soft magnetic part 123. The permanent magnets 122 and the soft magnetic parts 123 are arranged alternatively so that the like magnet poles face each other. When a soft magnetic body, so called attachment keeper, is placed in contact with the attachment 121, almost all magnetic flux pass along the keeper so that it is attracted to the attachment 121 quite firmly.

DISCLOSURE OF THE INVENTION

There is considerable demand for dental magnetic attachments to have an acceptable combination of stronger attractive force (more than 500 gram force) and small height (below 1.5 mm). The demand requires advanced technique in magnetics that improves the magnetic attractive force per unit volume F/V, that is, reduce the height without increasing the sectional area of the dental magnetic attachment. Since F/V in a given magnetic structure is determined by the characteristics of the material, it is difficult to improve F/V.

This invention is offered to solve the above mentioned problem, and offers an attachment with a combination of small height and strong attractive force, in other words, offers the means to increase the attractive force per unit volume F/V drastically.

First the structure of the invented attachment is described. Here 'height' is defined as a length taken along the direction of attraction, and 'thickness' is defined as a length taken along the direction normal to attraction.

The invented attachment consists at least three yokes and at least two pieces of magnet. The yokes are made of soft magnetic material, and a face of the yokes attaches to said keeper by magnetic attraction.

The magnets are sandwiched by the yokes. Their magnetization direction are parallel to the thickness-direction and the poles of each magnet which contact to the central yoke has like polarity. Each magnet form mutually independent magnetic circuit in which the magnetic flux generated at one pole of the magnet pass through one of two yokes in contact with the magnet, said keeper, and the other of said yokes and returns into the other pole of the magnet.

The ratio of $H/S^{1/2}$, in which H denotes the height of the magnet and S denotes the area of attracting face S, is not more than 0.55 with the attractive force of not less than 500 gf. It is preferable that $H/S^{1/2}$ is not more than 0.50.

The ratio of $TH/S^{1/2}$, in which TH denotes the total height of the magnet and keeper, is not more than 0.75, preferably not more than 0.70.

The invented attachment is used in a denture in similar manner to the existing ones which is embedded in the denture base so that it faces to the keeper embedded on the tooth root and act attractive force on it.

The present invention described above can have more than two pieces of magnet, although the structures with two or three pieces of magnet are preferable for the practical application, and more than three pieces of magnet are not required except for some particular cases. Keeping practical use in mind, typical structure with two pieces of magnet will be described below in detail.

The invented attachment with the typical structure consists of two pieces of magnets, the central yoke, and two outer yokes. The yokes are made of soft magnetic material. The magnets having their magnetization direction parallel to the thickness-direction are sandwiched by the central yoke and one of outer yokes. Two magnets are arranged to sandwich the central yoke while the like poles of the both magnets face each other. The whole assembly of the magnets and the central yoke are sandwiched by outer yokes.

As a consequence two magnetic circuits are formed in the attachment. One of the magnetic circuits is formed in which the magnetic flux generated by inner pole of the magnet passes through said central yoke, said keeper and said outer yoke, and returns to another pole of the magnet. Another magnetic circuit is formed in the other half of the attachment in a similar manner except it has counter direction of flux rotation.

The height of the keeper is preferably to be nearly equal to the thickness of the outer yoke. A keeper with reduced height does not create sufficient magnetic attracting force, on the other hand a keeper with increased height makes total height of the attachment large so that it can not meet the demand of small height for the attachment.

The magnetic characteristics of the material have great influence on the performance of the invented attachment. It is preferable to use the following materials. First the magnet should have the maximum energy product of not less than 20 MGOe, for example rare earth magnets. It is further preferable that the magnet has good corrosion resistance. Second, soft magnetic material for the yokes should have corrosion resistance with the saturation magnetization of not less than 13000 G and magnetic permeability of not less than 3000.

In the case that corrosive magnets are used, it is preferable to cover whole attachment with the corrosion-resistant coating to assure corrosion resistance of the invented dental attachment. Plated or sputtered coating of corrosion-resistant metal, resin coatings are the examples of the coating. The thickness of the coating is preferably to be 5–200 micro-meter thick. It is more desirable to cover exclusively the exposed magnet surface with the corrosion resistant coating except the face in contact with the yokes.

In order to prevent the magnet from corrosion perfectly, it is necessary to cover the magnets and yokes with the cap made of corrosion-resistant non-magnetic material except the attracting face of the attachment to the keeper, while cover the contact face, which is the one facing to the keeper, of the magnets with the spacer made of corrosion resistant non-magnetic material. The permeability of the material is preferably under 1.2. The cap and the spacers must be put tougher on the yokes by electron beam welding or laser welding to seal the magnet perfectly.

It is similarly preferable to cover the lateral faces, which faces are not in contact with the yokes, of the magnets with the corrosion resistant non-magnetic annular case.

Now the design parameters to reduce the volume of the attachment will be described. The square edge on the top of the outer yokes can be chamfered. It is because the chamfering makes the magnetic flux flow smoother and enhances the attractive force. Similarly, top face of the central yoke can have V-shaped groove for the same reason. In the case that the attachment is covered by corrosion-resistant cap, it should have similar shape to the yokes. In addition a bridge attached on the top of central yoke over the V-shaped groove may enhance fixation of the attachment to the denture.

Two magnetic circuits in the invented attachment bring a major merit of reducing the height of the attachment to a half of that of existing ones with single magnetic circuit. Furthermore the circuits enhance attractive force and reduce the central yoke thickness. The merits may be due to the following mechanism.

First the major merit concerning the attachment height will be described. The attractive force of the attachment is proportional to $B^2S$, here B denotes the magnetic flux density at the attracting face, S denotes the cross sectional area of the attracting face. In a case of given cross sectional area S and given kind of materials, B is determined by the pole area of the magnets as long as the magnetic flux leakage is negligible. A single magnet with a given pole area is equivalent to two magnets with a half pole area. It means that two magnets with a half height can replace for a single magnet with certain height, so that the two magnets give same attractive force as that of the attachments with single magnet. In other words the height of attachment is reduced to a half with a given attractive force.

Next other merits brought by the two magnetic circuits will be described. Generally a magnetic circuit consists of a permanent magnet which generates magnetic flux, soft magnetic material in which magnetic flux flows, and non-magnetic material which plays a role of barrier to the magnetic flux. In spite of the existence of the non-magnetic barrier, magnetic flux that flows in a magnetic circuit tend to leak to a certain extent. The leakage makes the effective flux density decrease and causes deterioration in attractive force.

Two magnetic circuits are formed when the invented attachment and the keeper 103 are set in contact as seen in FIG. 1. The magnetic flux which generated at the south pole of left-hand magnet 1 passes through the left-hand half of the central yoke 10, the left-hand half of the keeper 103, and the outer yoke 11 and returns to the pole. Thus the left-hand magnetic circuit is completed. In the same manner the right-hand magnetic circuit is formed. The magnetic flux which is generated at the south pole of the right-hand magnet 2 passes through the other half of the central yoke 10, the the other half of the keeper 103, and the right-hand outer yoke 12 and returns to the north pole of the magnet 2.

At the center plane of central yoke these two magnetic fluxes which are come from magnets on both sides run into collision and repel each other.

The repulsion by a magnetic circuit could form stronger barrier than non-magnetic barrier to the other magnetic circuit. It suppress the leakage from the central yoke for the other magnetic circuit and compress the flux to a higher density. As a consequence it brings a merit of stronger attractive force and the other merit that the central yoke requires less thickness than the total thickness of the outer yokes.

After the collision the magnetic fluxes inside the central yoke flow into the keeper and divide into two fluxes and run into the both outer yokes and returns to the outer side pole of the magnets. The formation of these complementary magnetic circuits give a compact attachment with strong magnetic attractive force.

Further, the formation of two magnetic circuits enable to reduce the height of the keeper to a half of existing ones, because the height of the keeper equals to the thickness of outer yokes, of which thickness is a half of that in existing attachment with single magnetic circuit. Thus the total height of dental attachment and the keeper can be reduced.

For the invented attachment the value of $H/S^{1/2}$, in which S denotes the area of the apparent attracting face and H denotes the magnet height measured from the attracting face, becomes not more than 0.55 with the attractive force of not less than 500 gram force. It means that the attachment can take a thin disc shape.

So far the reason that the invented attachment has desirable combination of small height H and strong attractive force has been described.

The principle is applicable to the attachment with magnets of three pieces or more. The height of the magnets are reduced to less than ⅓ when three magnets or more are used and three or more magnetic circuits are formed.

Similarly the thickness of the keeper for the invented attachment is less than ⅓ of those used in existing magnetic attachments.

The total area of poles of magnets used in present invention is nearly equal to that of single magnet used in the existing attachment shown in FIG. 25. Therefore the total flux in the present invention in which three magnets or more are used is equal to the flux in existing attachment with single large magnet. Because of it the attractive force of present invented attachment is nearly equal to that of existing attachment shown in FIG. 25. That is, present invented attachment has not less attractive force than that of existing ones in spite of its small height. For the practical application of this invention, two or three pieces of magnet are sufficient, and more than three pieces of magnet are not required except for some particular cases. However, It is possible to reduce the height further, for example the value of $H/S^{1/2}$ to be not more than 0.1, by increasing the number of magnet from 10 to 20. In those cases the attractive forces are also nearly equal to strong attractive force of existing dental attachments.

The previous inventions described before with FIG. 26, 27, which is disclosed in Japanese patent application Laid- Open (Kokai) No. 57-164054, has similar arrangement of magnets and yokes to the present invention. However the objective of the invention is to cover wide range of dentition and it does not improve the attractive force per unit volume of the attachment. In other words the height of the attachment is not reduced. On the contrary in present invention the height of the attachment is inverse-proportional to the number of magnets so that the attractive force per unit volume of the attachment is improved proportionally to the number of the magnets, which is the essential point of the present invention.

There is desirable dimensions of the present invented attachment to apply to teeth. It is preferable for the present invented dental attachment to have the attracting area of not more than 20.0 mm$^2$, more preferably not more than 14.0 mm$^2$, still more preferably 11.4 mm$^2$. When the attracting face has rectangular shape, it is preferable to have its longer side to be not more than 5.0 mm and its shorter side to be not more than 4.0 mm, more preferably not more than 4.2 mm and not more than 3.4 mm, respectively, still more preferably 3.8 mm and 3.0 mm, respectively.

As described above, the present invented dental attachment has strong attractive force with small height, in other words, increased F/V, attractive force per unit volume, to two times by adopting the structure with formation of two magnetic circuits. It should be noted that the present invention is no different from those of existing ones in the fixation with the denture, corrosion resistance or wear resistance.

When three magnets are used in this invention, the number of the magnetic circuits becomes three and F/V is further increased.

BRIEF DESCRIPTION OF THE FIGURES

FIG. 9 shows a cross sectional view of the dental attachment and the keeper disclosed as another modification of the embodiment 4.

FIG. 10 shows a cross sectional view of the dental attachment and the keeper disclosed yet another modification of the embodiment 4.

FIG. 21 shows a cross sectional view of the dental attachment and the keeper disclosed in embodiment 11.

FIG. 22 shows a cross sectional view of the dental attachment and the keeper disclosed in comparative sample 1.

Figure 1:
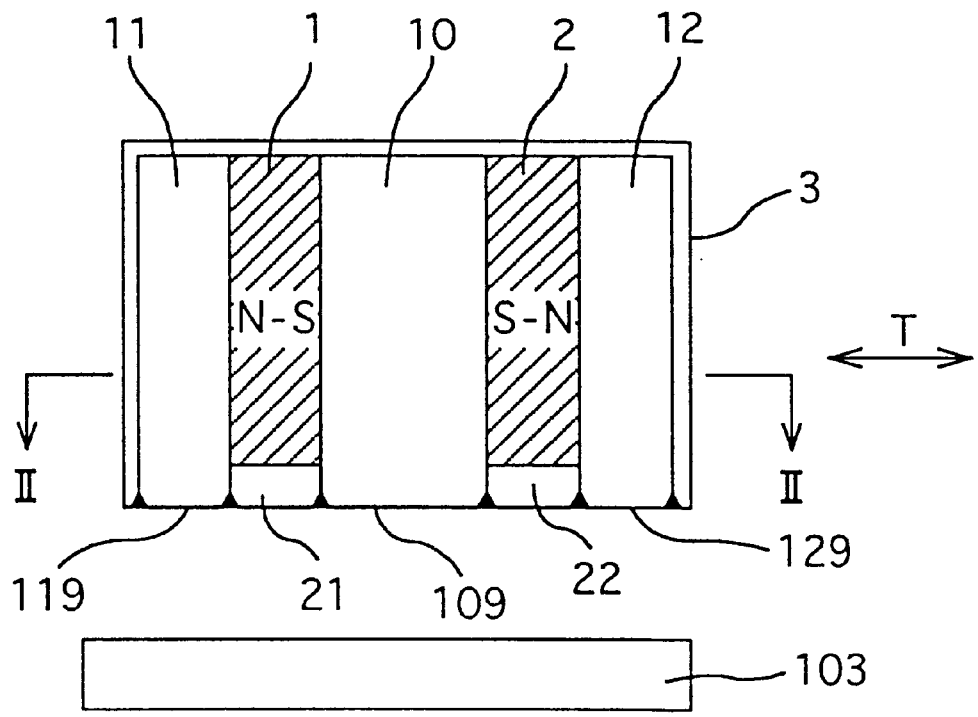
FIG. 1 shows a cross sectional view of the dental attachment and the keeper disclosed in embodiment 1.

DESCRIPTION OF NUMBERED ITEMS 1 magnet
2 magnet
3 cap
4 bridge
5 case
10 central yoke
109 central attracting face
11 outer yoke
119 first attracting face
12 outer yoke
129 second attracting face
21, 22 spacer
51, 52 case part
101 tooth root
102 root surface
103 keeper
110 denture
111 dental attachment
112 magnet in the existing attachment
113 spacer in the existing attachment
114, 115 yokes in the existing attachment
116 cap in the existing attachment
T direction of thickness

THE BEST MODE OF THE INVENTION

The embodiments of the present invention will be described below with figures.

(Embodiment 1)

Figure 2:
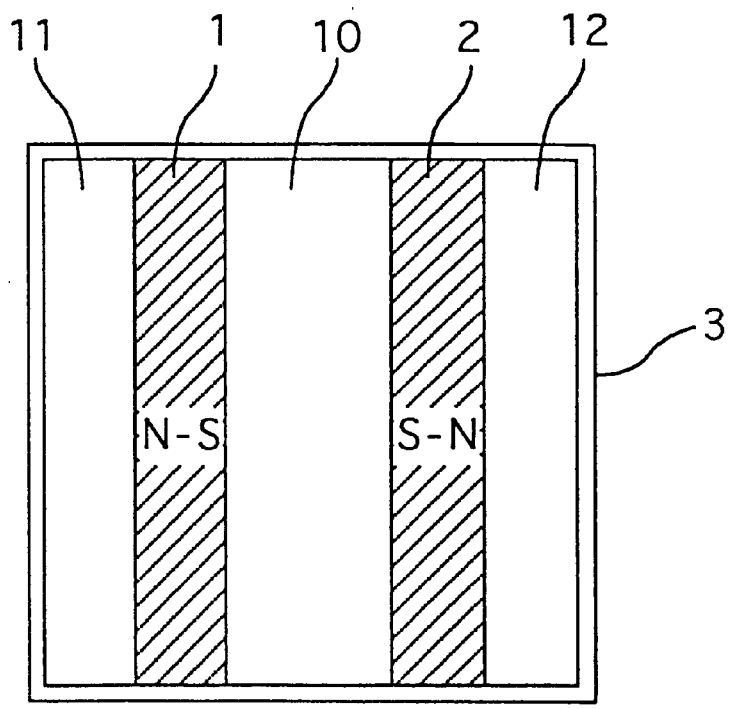
FIG. 2 shows a horizontal sectional view of the dental attachment disclosed in embodiment 1.

A cross sectional view of the dental attachment in embodiment 1 of the present invention is shown in FIG. 1, and horizontal sectional view in FIG. 2. This attachment has a central yoke 10 in which one of the faces parallel to the direction of thickness T is the magnetic attracting face 109 to the keeper 103.

The magnet 1 having its magnetization direction parallel to the direction of the thickness T is placed in contact with the central yoke 10. The magnet 2 having its magnetization direction parallel to the direction of the thickness T is placed in contact with another face of the central yoke 10 so that the like poles of the magnet 1 and the magnet 2 face each other. The outer yoke 11 is placed in contact with another face of the magnet 1, which is the opposite face to the one in contact with the central yoke 10, and one of its face parallel to the direction of the thickness T forms the attracting face 119 to the keeper 103. The outer yoke 12 is also placed in contact with another face of the magnet 2, which is the opposite face to the one in contact with the central yoke 10, and one of its face parallel to the direction of the thickness T forms the attracting face 129 to the keeper 103.

The central yoke 10, the magnet 1, the magnet 2, the outer yoke 11, another outer yoke 12 are enclosed in the cap 3 made of non-magnetic alloy. The face to the keeper 103, namely, central attracting face 109, the attracting face 119, and the attracting face 129 are exposed at opening of the cap 3. The attracting faces of the magnet 1 and magnet 2 with the keeper 103 are covered with spacer 21, 22 made of non-magnetic alloy.

The boundary of attracting face on the cap 3, spacer 21, 22, central yoke 10, the outer yoke 11, and another outer yoke 12 are welded hermetically by electron beam welding or laser welding so that saliva does not come inside the cap 3 and corrode the magnet.

(Table 1)

In the present embodiment 1, one of the magnetic circuits is formed in the magnet 1, the central yoke 10, the keeper 103, and the outer yoke 11. Similarly the other of the magnetic circuits is formed in the magnet 2, the central yoke 10, the keeper 103, and the outer yoke 12. In order to pass the two magnetic fluxes in parallel, the central yoke 10 has 1.57 times larger thickness of that of outer yoke 11, 12. These two magnetic circuits give strong attractive force twice as much as the force of existing dental attachments. The obtained attractive force is 607 gf, larger than 500 gf necessary for dental attachment. $H/S^{1/2}$, in which S denotes the area of attracting face and H denotes the height from the attracting face, equals to 0.45. It is below the value of 0.55 stipulated in former section as a characteristic of the present invention. $TH/S^{1/2}$, in which T denotes the total height of the keeper and the attachment, equals to 0.69, and below the value of 0.75 stipulated in former section as a characteristic of the present invention.

(Embodiment 2)

The attachment in the embodiment 2 has same structure with same material as embodiment 1 as shown in table 2, however the dimensions of the parts are modified. By the modification the attractive force has increased to 618 gf although cross sectional area also increased a little. $H/S^{1/2}$ and $TH/S^{1/2}$ of the embodiment 2 equal to 0.42 and 0.47, respectively.

(Table 2)

(Embodiment 3)

The attachment in the embodiment 3 has same structure with same material however the thickness is increased in order to decrease the height to 1.3 mm for the magnet 1 and magnet 2 as shown in table 3. By the modification the attractive force showed 564 gf. $H/S^{1/2}$ and $TH/S^{1/2}$ of the embodiment 3 equal to 0.37 and 0.58, respectively.

(Table 3)

(Embodiment 4)

Figure 3:
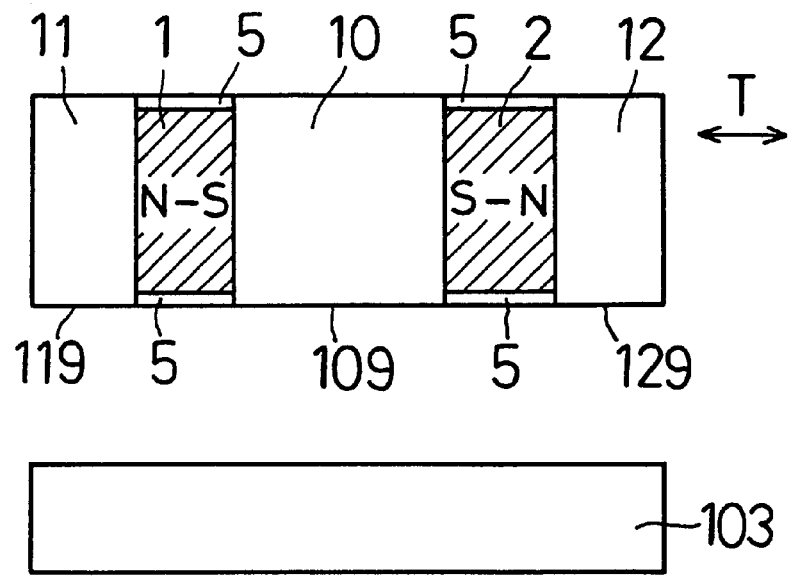
FIG. 3 shows a cross sectional view of the dental attachment and the keeper disclosed in embodiment 4.
Figure 4:
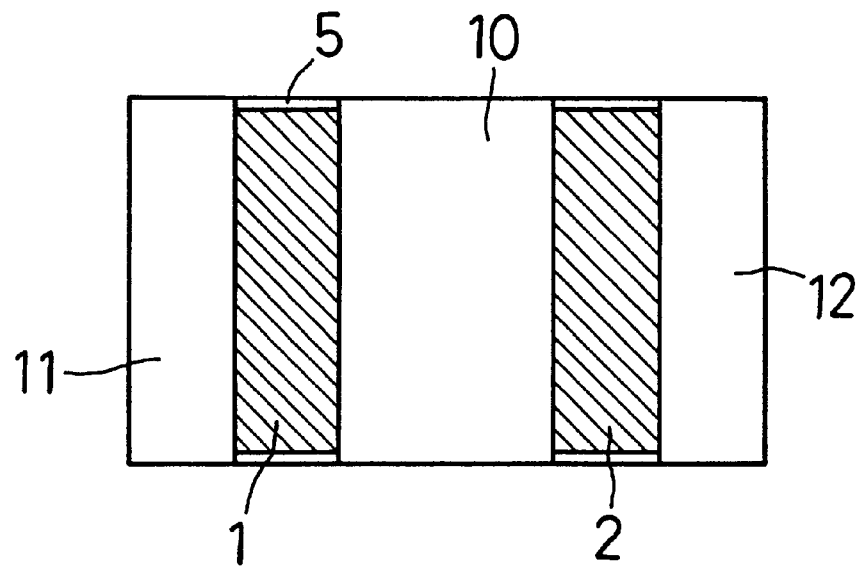
FIG. 4 shows a cross sectional view of the dental attachment disclosed in embodiment 4.
Figure 5:
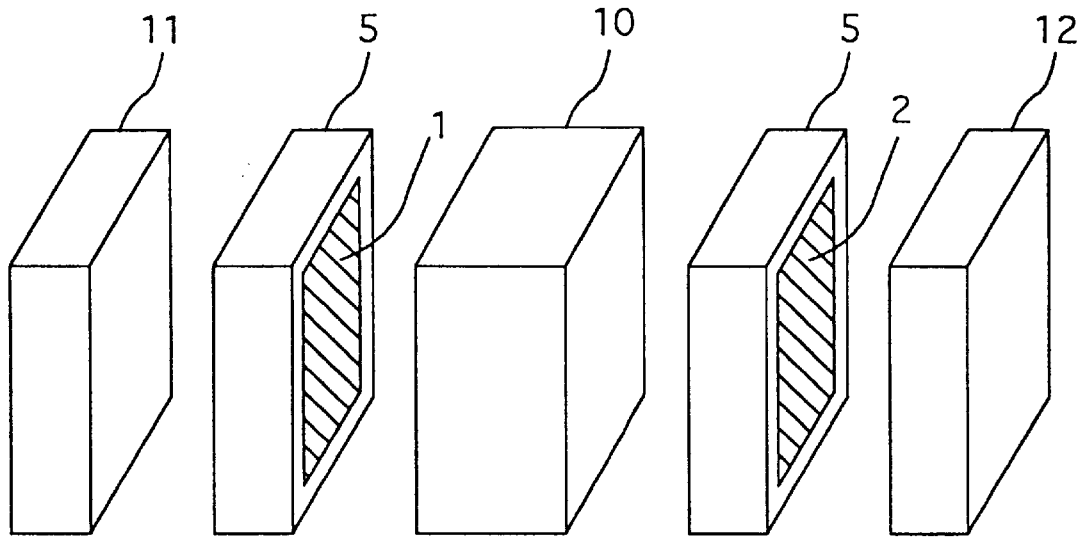
FIG. 5 shows an exploded view of the dental attachment disclosed in embodiment 4.

The attachment in embodiment 4 has different structure from embodiment 1–3 described above. As shown cross sectional view in FIG. 3, horizontal sectional view in FIG. 4, and exploded view in FIG. 5, the lateral face of the magnet 1, namely the face not in contact with the central yoke 10 nor the outer yoke 11, is covered by annular case 5 made of corrosion resistant non-magnetic material. Similarly the lateral face of the magnet 2, namely the face not in contact with the central yoke 10 nor the outer yoke 12, is covered by similar annular case 5 made of corrosion resistant non-magnetic material. The attachment does not have the case covering the magnet 1, magnet 2, and yokes 10, 11, 12, neither does not have spacers covering the attracting face of the magnets.

The contacting part of case 5 and yokes 10, 11, 12 are welded hermetically by electron beam welding or laser welding so that saliva does not come inside and corrode the magnet.

Figure 6:
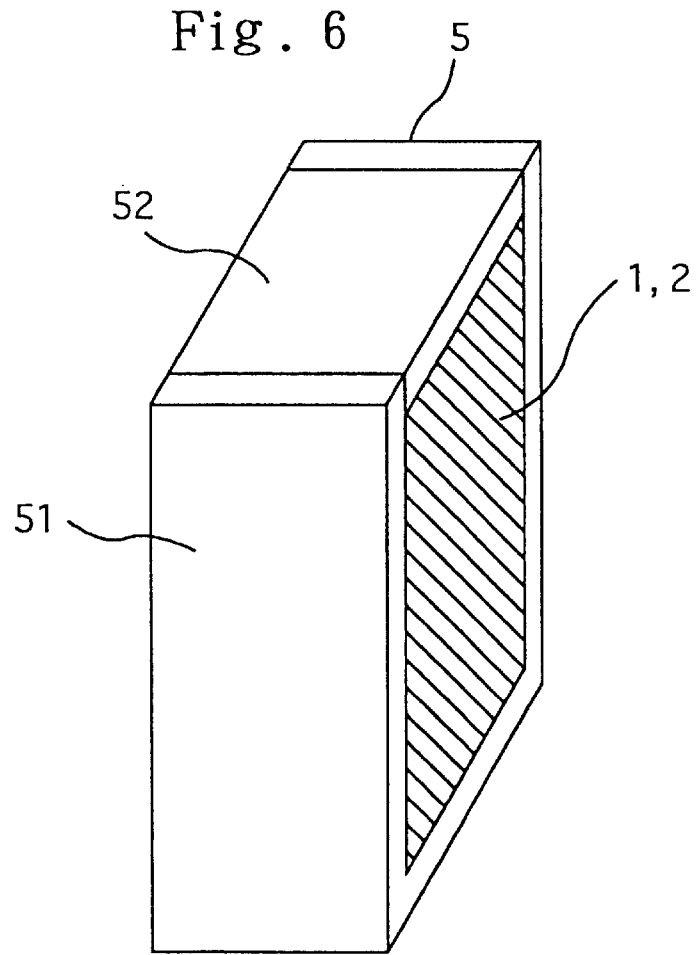
FIG. 6 shows the structure of the case in embodiment 4.

The case 5 consists of U-shaped part 51 that enclose the magnet 1 or magnet 2 and flat plate part 52 that covers the top face of the magnets as shown in FIG. 6. They are welded together hermetically by electron beam welding or laser welding.

The structure of the case 5 is not restricted by the above mentioned one. Two U-shaped parts can be butt-welded together, or four flat plates can be welded at the ends to form the case, or one plate can be bent annularly and both ends are butt-welded together, or annular case can be formed as one body and the magnet is inserted in the opening.

In any structure the case 5 should be made of as low permeability material as possible and thickness should be as thin as corrosion resistance and weldability permit in order to obtain strong attractive force of magnetic attachment.

The dimensions and magnetic characteristics and kinds of material of the parts used in the embodiment 4 are shown in table 4. There is no cap nor spacer as is in the former embodiments, but case 5 is added. It showed 590 gf of attractive force in spite of decreased cross sectional area of 9.8 mm², although the height is increased a little to 1.6 mm. $H/S^{1/2}$ and $TH/S^{1/2}$ of the embodiment 4 equal to 0.51 and 0.73, respectively.

(Table 4)

Figure 7:
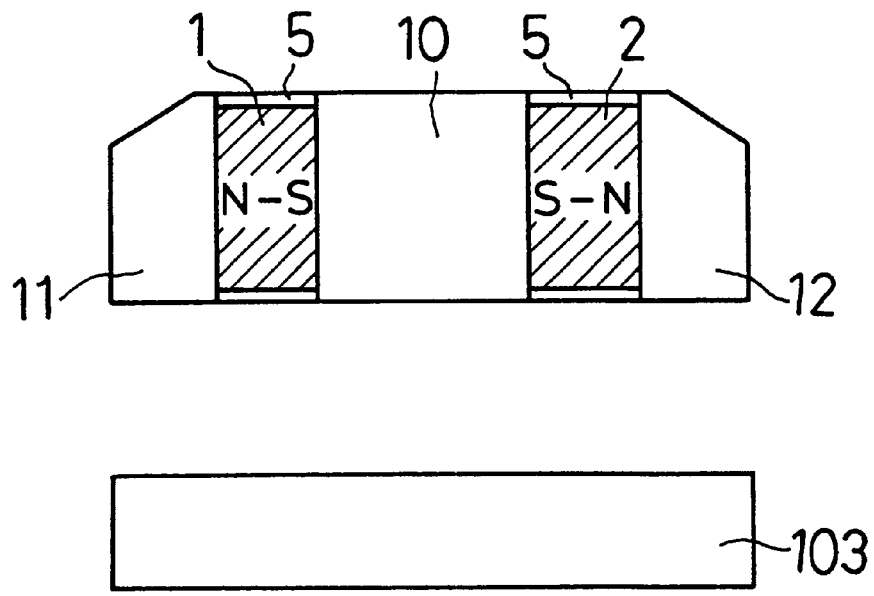
FIG. 7 shows a cross sectional view of the dental attachment and the keeper disclosed as the modification of the embodiment 4.
Figure 8:
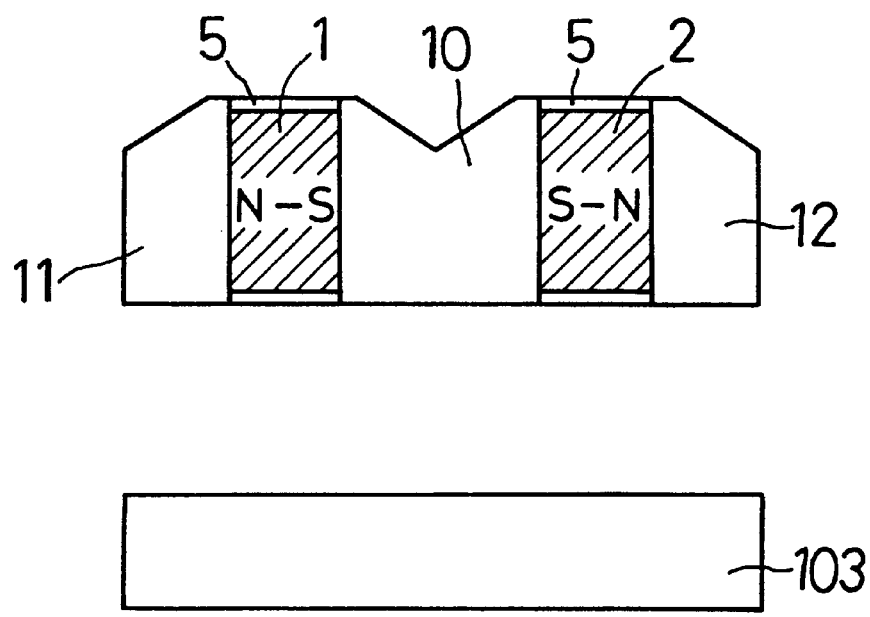
FIG. 8 shows a horizontal sectional view of the dental attachment disclosed as the modification of the embodiment 4.

As a modification of embodiment 4, the outer upper side of the outer yoke 11 and the outer yoke 12 can be chamfered as cross sectional view is shown in FIG. 7. Also as shown in FIG. 8 the top face of the central yoke 10 can have V-shaped groove. The chamfering makes the magnetic flux flow smoother and enhances the attractive force.

Figure 11:
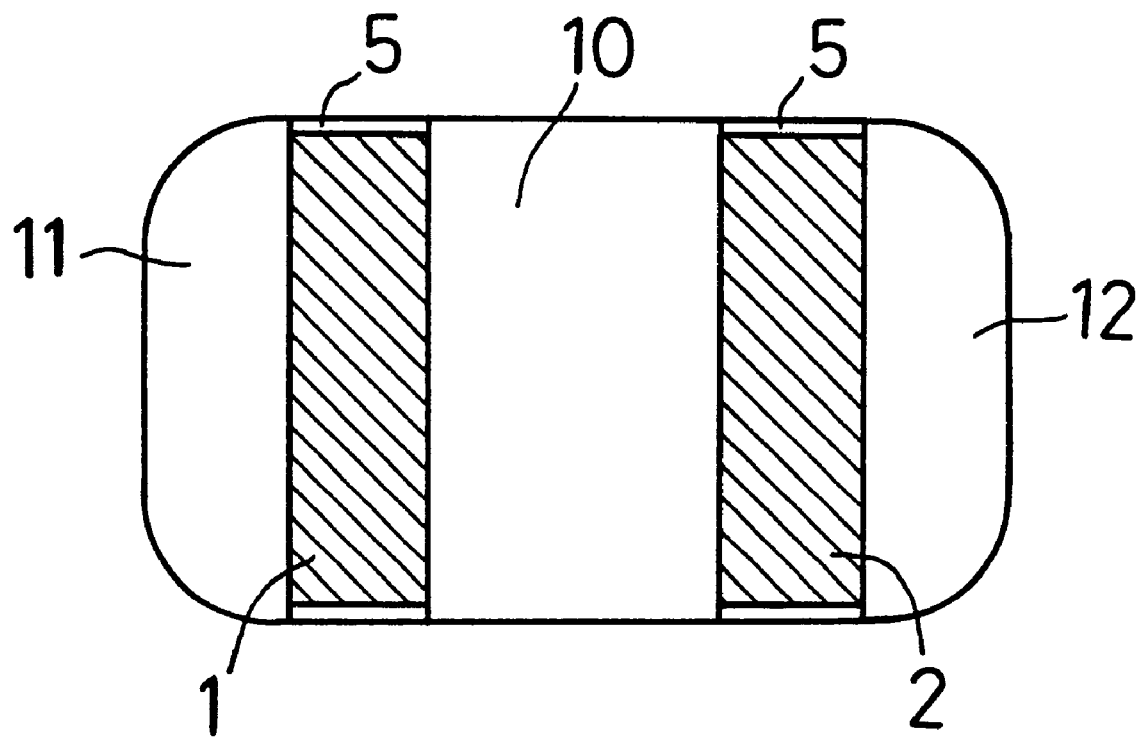
FIG. 11 shows a horizontal sectional view of the dental attachment disclosed as modification of the embodiment 4.

In addition the outer yoke 11 and the outer yoke 12 can have a groove on their sides as shown in FIG. 9 and FIG. 10. This groove plays a role of anchor for the fixation of attachment to the denture. Dental resin fills the groove and the attachment is fixed firmly on the denture. Stripes on the surface of the attachment also effective for the fixation. Further, the four corners of the outer yoke 11 and the outer yoke 12 can be chamfered as shown in horizontal view in FIG. 11.

(Embodiments 5)

Figure 12:
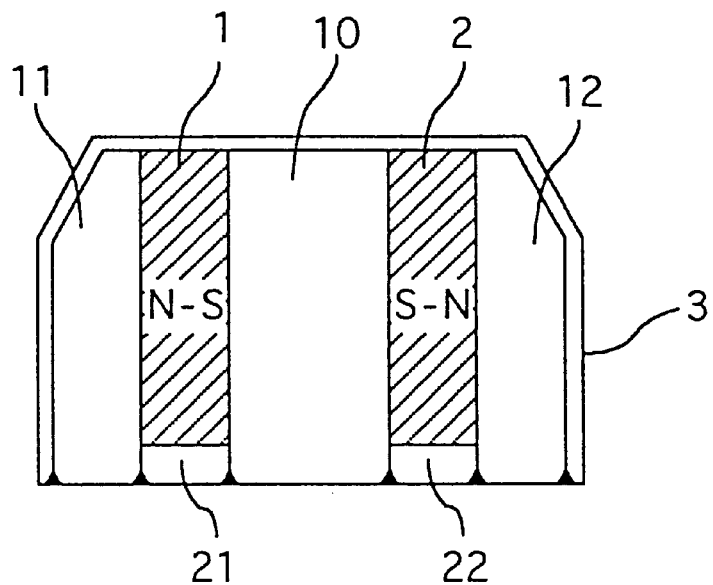
FIG. 12 shows a cross sectional view of the dental attachment disclosed in embodiment 5.

The attachment in the embodiment 5 has same structure and same material with same magnetic characteristics as embodiment 1 however the outer yokes 11 and 12 are chamfered at the outer top side as shown in FIG. 12. By the modification the volume of the attachment is reduced, and fitting to the denture is improved.

It has an attractive force of 603 gf, which compare favorably with that of 607 gf obtained by the embodiment 1.

H/S$^{1/2}$ and TH/S$^{1/2}$ of the embodiment 3 equal to 0.45 and 0.66, respectively.
(Table 5)
(Embodiment 6)

Figure 13:
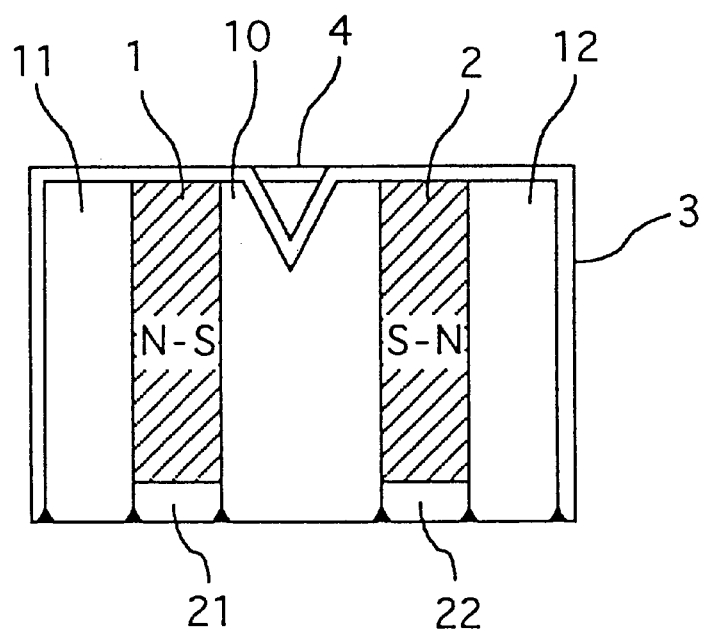
FIG. 13 shows a cross sectional view of the dental attachment disclosed in embodiment 6.

The attachment in the embodiment 6 has same structure and same material with same magnetic characteristics as embodiment 1. The specifications are shown in table 6. The central yoke 10 is chamfered at the top face and a bridge 4 is placed to enhance the fixation with the denture as shown in FIG. 13. The bridge can be plurality of stick-shaped ones or plate with plurality of punched holes. The central yoke is so chamfered that it makes the magnetic flux flow smoother. The attractive force showed 601 gf. H/S$^{1/2}$ and TH/S$^{1/2}$ of the embodiment 6 equal to 0.45 and 0.66, respectively.
(Table 6)
(Embodiment 7)

The attachment in the embodiment 7 uses different materials for the magnet 1, the magnet 2, spacers 21, 22 and cap 3. It showed the maximum attractive force of 666 gf. H/S$^{1/2}$ and TH/S$^{1/2}$ of the embodiment 7 equal to 0.45 and 0.69, respectively.
(Table 7)
(Embodiment 8)

The attachment in the embodiment 8 has same structure and dimensions as embodiment 1 however iron-cobalt alloy (a typical commercial alloy is Permendur) with the saturation magnetization of 24000 G is used for the material of the yokes 10, 11 and 12 as shown in table 8. By the modification the attractive force increased drastically to 1017 gf, the strongest in the embodiments disclosed in this application. H/S$^{1/2}$ and TH/S$^{1/2}$ of the embodiment 3 equal to 0.45 and 0.63, respectively.

In this embodiment the attracting face of the attachment is coated with high chromium-content alloy layer with the thickness of 20 micro-meters to protect the alloy from corrosion.
(Table 8)
(Embodiment 9)

The attachment in the embodiment 9 has same structure and dimensions as embodiment 1 however pure iron with the saturation magnetization of 22000 G and permeability of 10000 is used for the material of the yokes 10, 11, 12 and the keeper 103 as shown in table 9. By the modification the attractive force showed 818 gf, the next strongest in the embodiments disclosed in this application. H/S$^{1/2}$ and TH/S$^{1/2}$ of the embodiment 3 equal to 0.45 and 0.63, respectively.

In this embodiment the attracting face of the attachment is coated with high chromium content alloy layer with the thickness of 20 micro-meters to protect the alloy from corrosion.
(Table 9)

Figure 14:
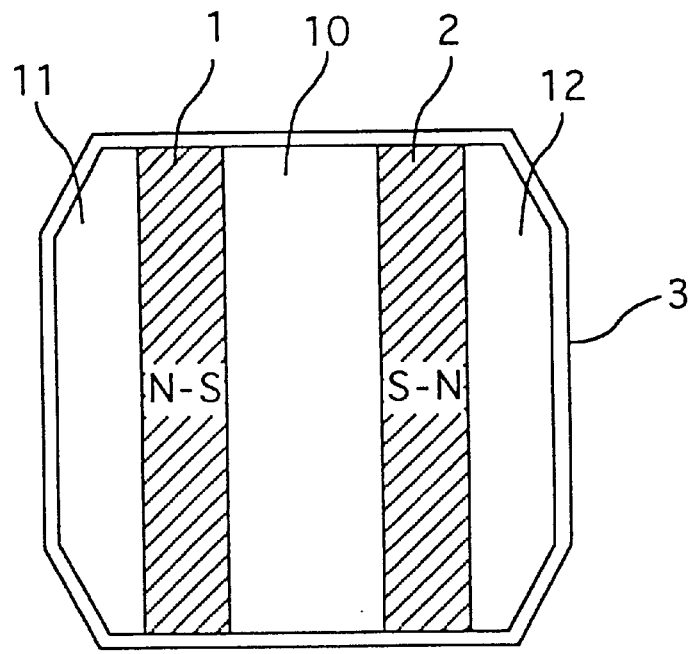
FIG. 14 shows an example of horizontal sectional view of the present invention.
Figure 15:
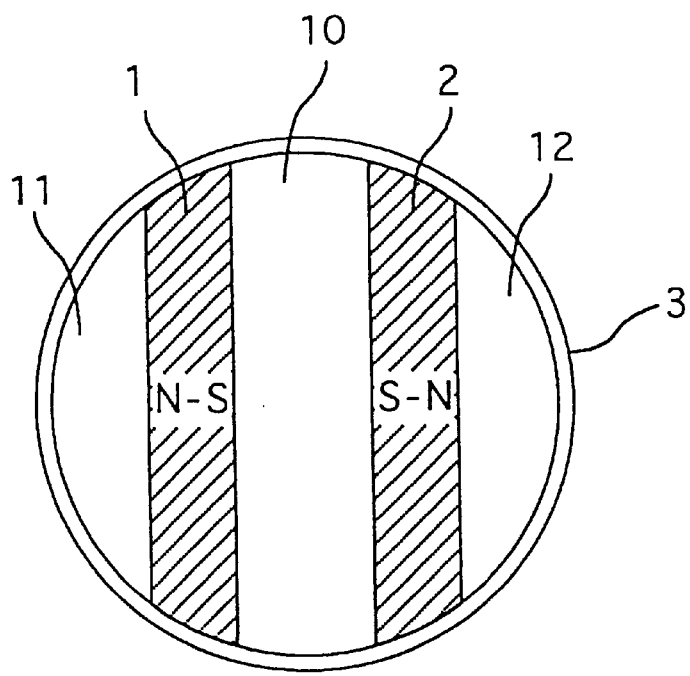
FIG. 15 shows an example of horizontal sectional view of the present invention.

The embodiments described above have rectangular horizontal cross section as shown in FIG. 2. However the design can be modified so that it can fit to the denture. For example chamfering the corner as shown in FIG. 14, round shape as shown in FIG. 15, or polygon, eclipse, pseudo-circle can be adopted for the cross sectional shape of the attachment.

Similarly three-dimensional shape can be modified. For example the corner of the both side yokes 11, 12 are cut away to have the cross sectional shape of triangle. Trapezoid or tapered shape of the attachment is also acceptable.
(Embodiment 10)

Figure 19:
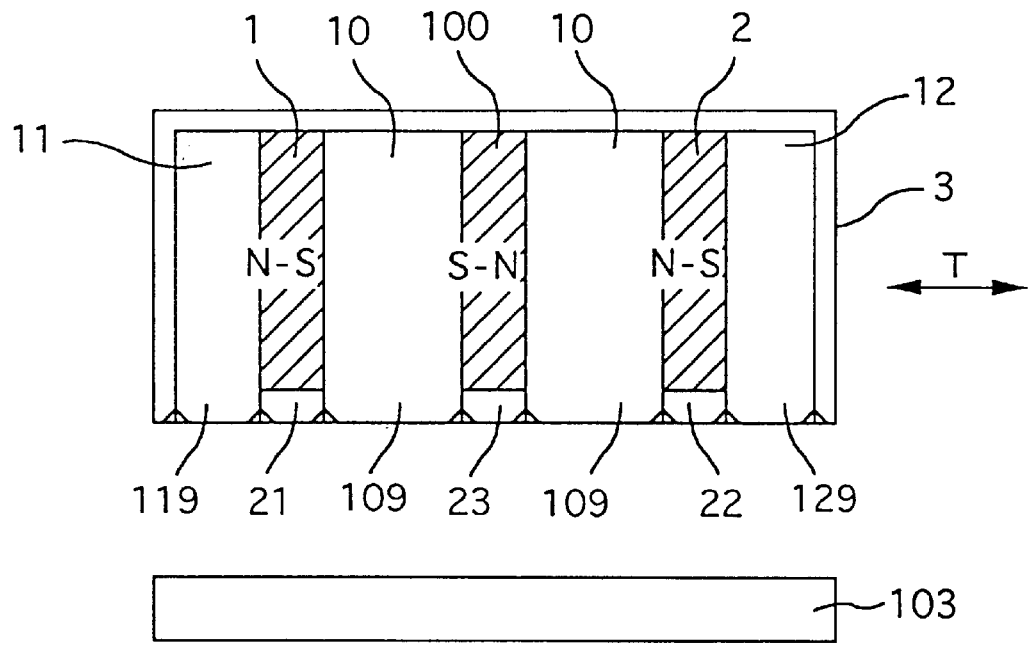
FIG. 19 shows a cross sectional view of the dental attachment and the keeper disclosed in embodiment 10.
Figure 20:
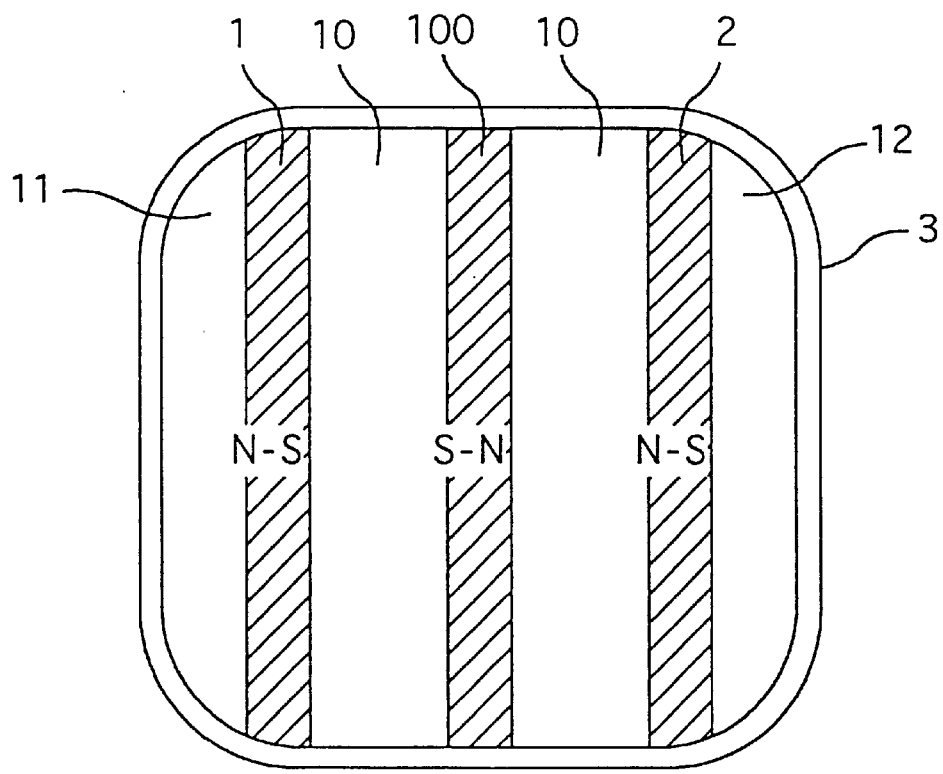
FIG. 20 shows a horizontal sectional view of the dental attachment disclosed in embodiment 10.
Figure 23:
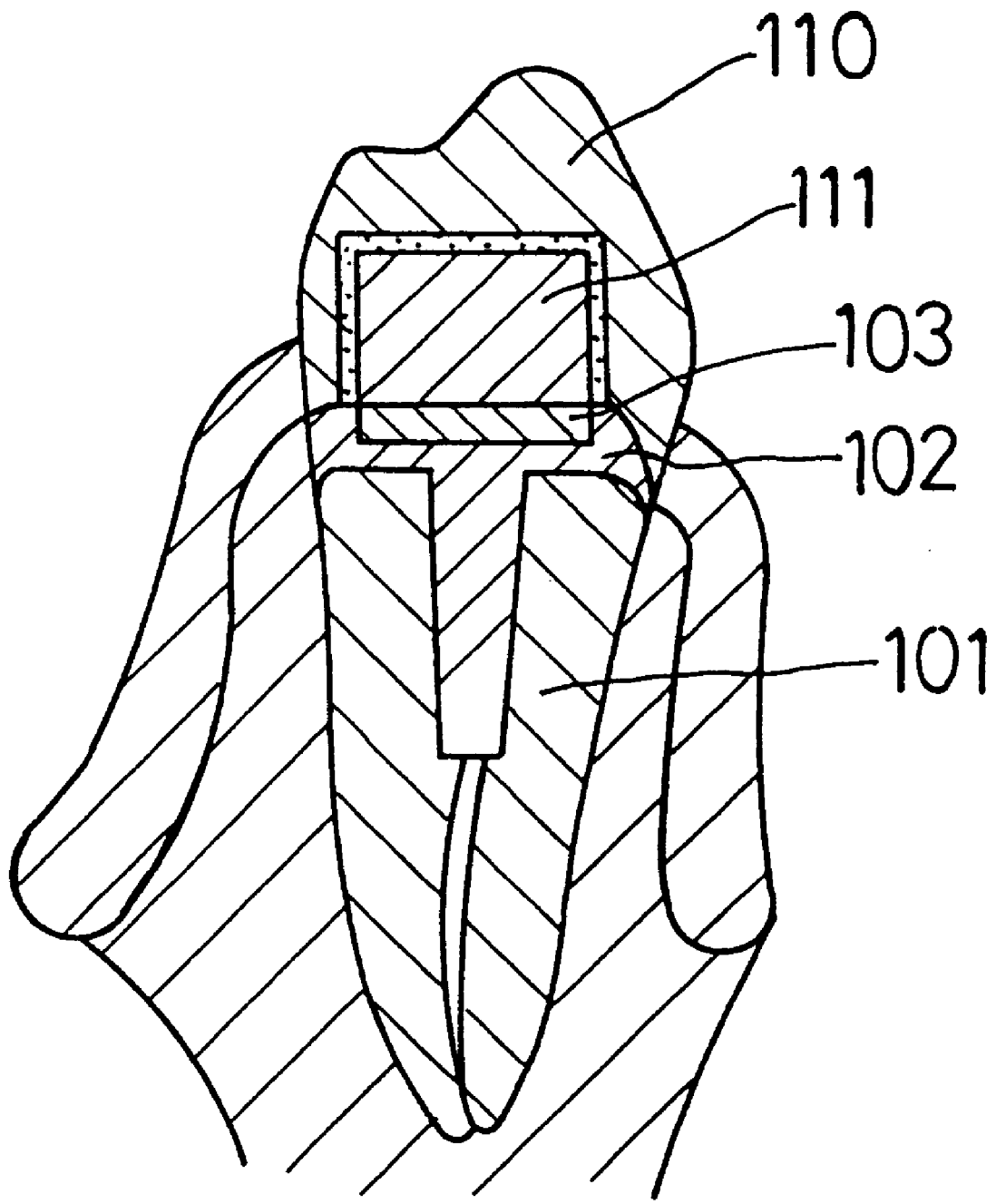
FIG. 23 shows a cross sectional view of the denture retention by a dental attachment.
Figure 24:
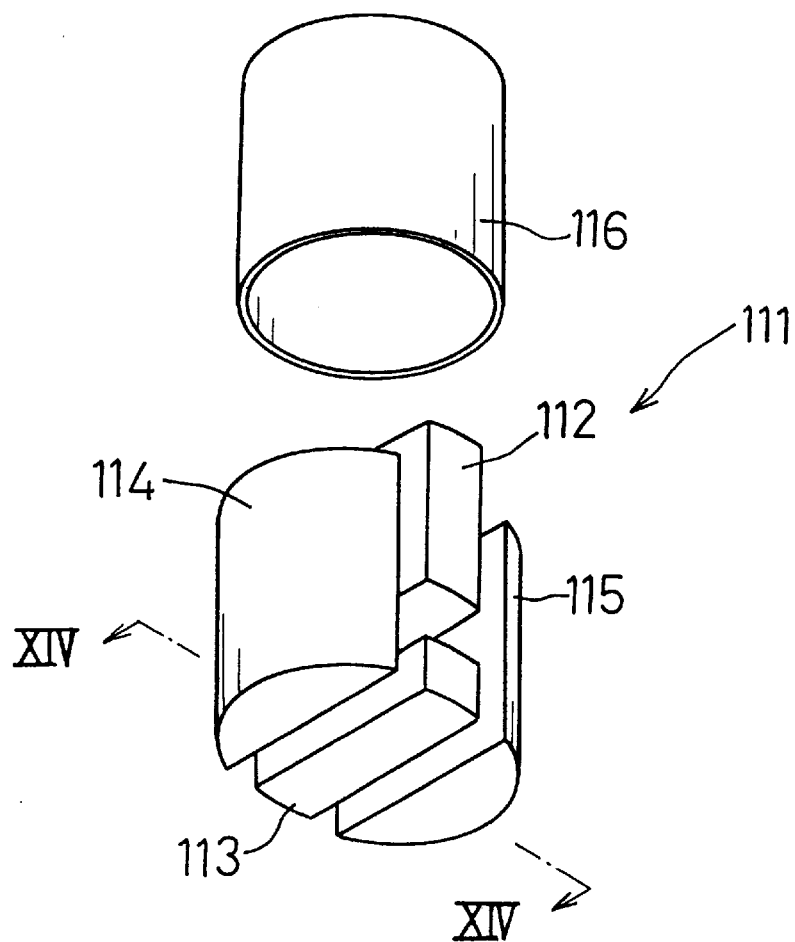
FIG. 24 shows an exploded view of the existing dental attachment.
Figure 25:
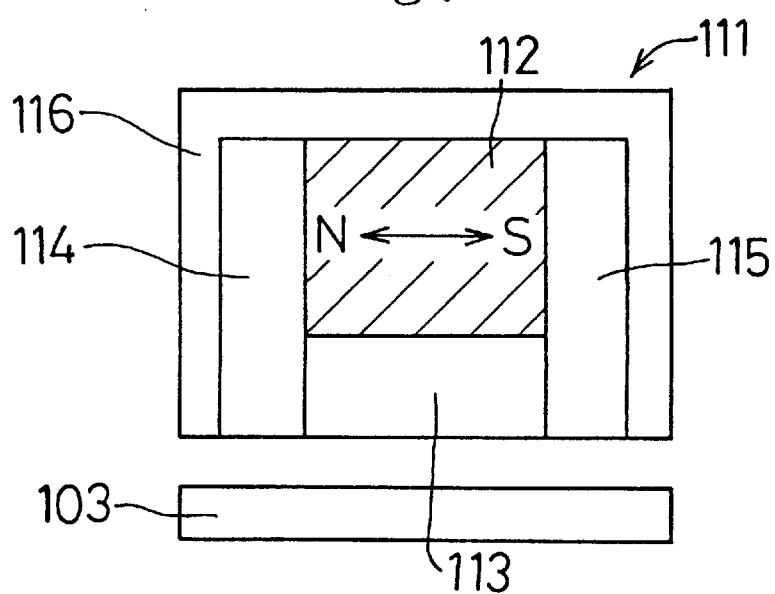
FIG. 25 shows a cross sectional view of the existing dental attachment.
Figure 26:
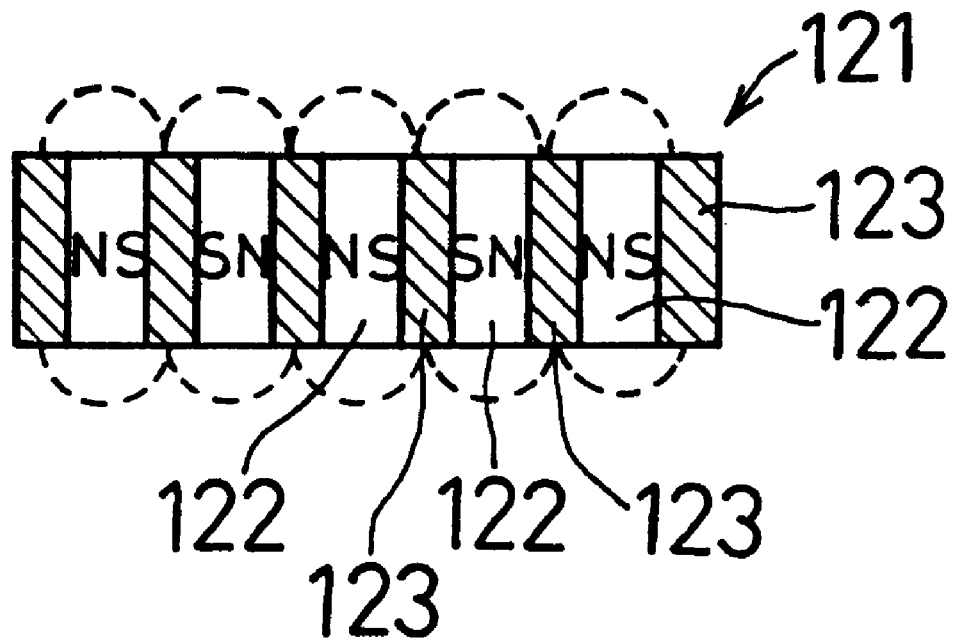
FIG. 26 is a schematic drawing showing the magnetic circuit and the combination of permanent magnet and soft magnetic body in the existing dental attachment.
Figure 27:
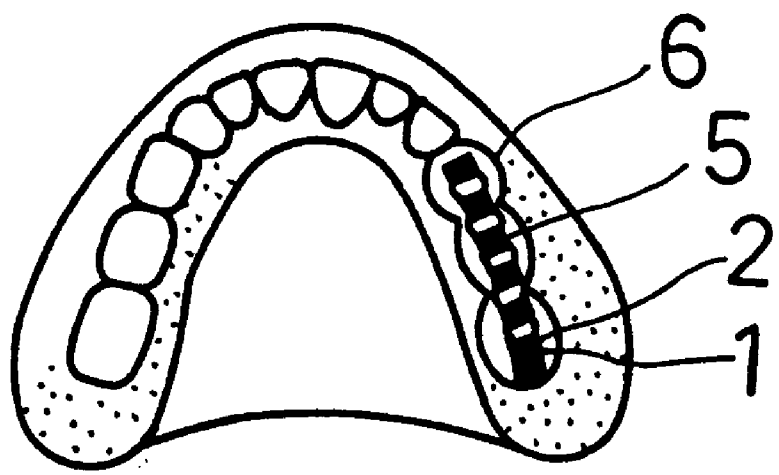
FIG. 27 shows the bottom view of the dental attachment of FIG. 26 used in the denture.

A cross sectional view of the dental attachment in embodiment 10 is shown in FIG. 19, and horizontal sectional view in FIG. 20. This attachment has two central yokes 10 in which one of the faces parallel to the direction of thickness T is the magnetic attracting face 109 to the keeper 103.

The central magnet 100 having its magnetization direction parallel to the direction of the thickness T is sandwiched by two central yokes 10 from both faces. The magnet 1 having its magnetization direction parallel to the direction of the thickness T is placed in contact with the other face of central yoke 10 so that the like poles of the magnet 1 and the central magnet 100 face each other. The magnet 2 having its magnetization direction parallel to the direction of the thickness T is placed in contact with another central yoke 10 so that the like poles of the magnet 2 and the central magnet 100 face each other. The outer yoke 11 is placed in contact with another face of the magnet 1, which is the opposite face to the one in contact with the central yoke 10, and one of its face parallel to the direction of the thickness T forms the attracting face 119 to the keeper 103. The outer yoke 12 is also placed in contact with another face of the magnet 2, which is the opposite face to the one in contact with the central yoke 10, and one of its face parallel to the direction of the thickness T forms the attracting face 129 to the keeper 103.

The central yokes 10, the magnet 1, the magnet 2, the outer yoke 11, the outer yoke 12 are enclosed in the cap 3 made of non-magnetic alloy. The face to the keeper 103, namely, central attracting face 109, the attracting face 119, and the attracting face 129 are exposed at opening of the cap 3. The attracting faces of the magnet 1 and magnet 2 with the keeper 103 are covered with spacer 21, 22 made of non-magnetic alloy.

The boundary of attracting face of the cap 3, spacer 21, 22, central yoke 10, the outer yoke 11, the outer yoke 12 are welded hermetically by electron beam welding or laser welding so that saliva does not come inside the cap 3 and corrode the magnet.

The shape, magnetic properties and materials for the parts of the dental attachment in embodiment 10, namely the central magnet 100, the magnets 1, 2, the outer yokes 11, 12, the central yoke 10, 10, spacer 21, 22, 23, the cap 3, and keeper 103 are shown in table 17.
(Table 10)

In the present embodiment 10, the first magnetic circuit is formed in the magnet 1, one of the central yoke 10, the keeper 103, and the outer yoke 11. Similarly the second magnetic circuit is formed in the central magnet 100, one of the central yoke 10, the keeper 103, and the other central yoke 10. Similarly the third magnetic circuit is formed in the magnet 2, one of the central yoke 10, the keeper 103, and the outer yoke 12. In order to pass the two magnetic fluxes in parallel, the central yoke 10, 10 have 1.66 times larger thickness of that of the outer yoke 11 or outer yoke 12. These three magnetic circuits give strong attractive force and require less height for the attachment. The obtained attractive force is 515 gf, larger than 500 gf necessary for dental attachment, with the height of only 1.03 mm. H/S$^{1/2}$, in which S denotes the area of attracting face and H denotes the height from the attracting face, equals to 0.31. It is below the value of 0.55 stipulated in former section as a characteristic of the present invention. TH/S$^{1/2}$, in which T denotes the total height of the keeper and the attachment, equals to 0.44, and below the value of 0.75 stipulated in former section as a characteristic of the present invention.
(Embodiment 11)

The attachment in embodiment 11 has similar structure as embodiment 4. It consists of the magnet 1, the magnet 2, the central yoke 10, the outer yoke 11, and the outer yoke 12 as shown cross sectional view in FIG. 21, without the cap and spacers covering the attracting face of the magnets. It uses Nd14Fe77B8, a magnet with very high maximum energy product, as the magnet material similar to embodiment 7 in order to reduce the volume. In other words, the present embodiment applies a combination of the structure of the embodiment 4 and the magnet material of the embodiment 7. Because of the structure and the material, the obtained attractive force is 620 gf, larger than 500 gf necessary for dental attachment, without increasing the number of the magnet more than 3. It also achieves the height of only 1.2 mm. $H/S^{1/2}$ equals to 0.39, below the value of 0.55 stipulated in former section as a characteristic of the present invention. $TH/S^{1/2}$ equals to 0.58, below the value of 0.75 stipulated in former section as a characteristic of the present invention.
(Table 11)

Next, one comparative example and four existing example are described to show the superiority of the present invention.
(Comparative Example 1)

The cross sectional view of the dental attachment in comparative example 1 is shown in FIG. 22. It is prepared to compare the dental attachment in embodiment 11 with two magnets to the existing dental attachment with one magnet.

The comparative example is designed to have the attractive force of 620 gf, same as the one in the embodiment 11. Dimensions of the parts of the comparative example 1 are shown in table 12. The height of the attachment is 2.4 mm and the thickness of the keeper is 1.2 mm as shown in table 12. $H/S^{1/2}$ equals to 0.78, larger than the value of 0.55 below which is a characteristic of the present invention. $TH/S^{1/2}$ is 1.16, larger the value of 0.75 below which is another characteristic of the present invention.

As seen from comparison for the dental attachment in comparative example 1 and the embodiment 11, the present invention gives much smaller height and smaller total height indicated by $H/S^{1/2}$ and $TH/S^{1/2}$ for a given attractive force.
(Existing Example 1)

This example is the one found in the market currently. Hereafter it is referred as attachment A. This existing attachment consists of a block of magnet 112, a spacer 113 made of corrosion resisting non-magnetic alloy and covers one surface of the magnet, a pair of yokes 114, 115 that made of corrosion resisting soft magnetic alloy and sandwich the magnet 112 and the spacer 113 in between, and a cap 116 made of corrosion resisting non-magnetic alloy and covers whole other parts. It has a structure of a magnet sandwiched by two yokes. The dimension and material used in each part is shown in table 13. It has a height of 2.5 mm, a cross sectional area of 12.0 mm². Its height is much larger compared to the average height of 1.5 mm for the present embodiments although the attractive force of 605 gf is similar to them. The height limits the application of the attachment. Its $H/S^{1/2}$ and $TH/S^{1/2}$ equal to 0.72 and 1.01 respectively and considered to be rather large.
(Table 13)
(Existing Example 2)

This example is another one found in the market currently. Hereafter it is referred as attachment B. This existing attachment has similar structure to existing example 1 except reduced height of 1.5 mm as shown in table 14. Because of the reduced height, the attractive force is decreased to 400 gf, which is not sufficient as a dental attachment.
(Table 14)
(Existing Example 3)

This example is yet another one found in the market currently. Hereafter it is referred as attachment C. The dimension and material used in each part is shown in table 15. This example has a particular structure in which cylindrical magnet is placed so that one pole is facing to the keeper and the magnetic flux generated at the other pole is lead by a cup-shaped yoke to the keeper. It shows only 352 gf of attractive force in spite of rather large cross sectional area of 12.6 mm². It is inferior even to the existing example 2 described before.
(Table 15)
(Existing Example 4)

The dental attachment as existing example 4 has a structure of a magnet sandwiched by two yokes. As dimension and material used in each part is shown in table 16, it has same cross sectional area and same material for the parts of the present embodiment 1. The magnet has a thickness equals to the total of the magnet 1 and the magnet 2 in the embodiment 1. Thus it gives comparative example for the present invention utilizing multiple piece of magnet.

The example has only 335 gf of attractive force, far below that of obtained by the present invention. It is because the example has only one magnetic circuit, while the present invention has two or more magnetic circuits.
(Table 16)

In table 17 the attractive force (gf), attractive force per unit volume F/V (gf/mm²), the height (mm), and cross sectional area (mm²) of the attachment are shown for all of the eleven embodiments, one comparative example and four existing examples.
(Table 17)

The embodiment 8 is the most superior one in both the attractive force and the attractive force per unit volume. The embodiment 9 has the second best performance following to the embodiment 8 in spite of using inexpensive pure iron without using the special alloy such as iron-cobalt-vanadium. The embodiment 3 has showed that the height can be reduced to 1.3 mm, the embodiment 4 has showed that the cross sectional area can be reduced to 9.8 mm² to obtain the attractive force more than 500 gf, a requirement for a dental attachment. The embodiment 10 has showed that the height can be even reduced by using three pieces of magnet. In the embodiment 11 very small height of $H/S^{1/2}$ 0.39 and $TH/S^{1/2}$ of 0.58 with the attractive force of 620 gf is obtained.

For each embodiment, the value of $H/S^{1/2}$ is below 0.51, satisfying the stipulation for the present invention to be below $H/S^{1/2}$ of 0.55.

Figure 16:
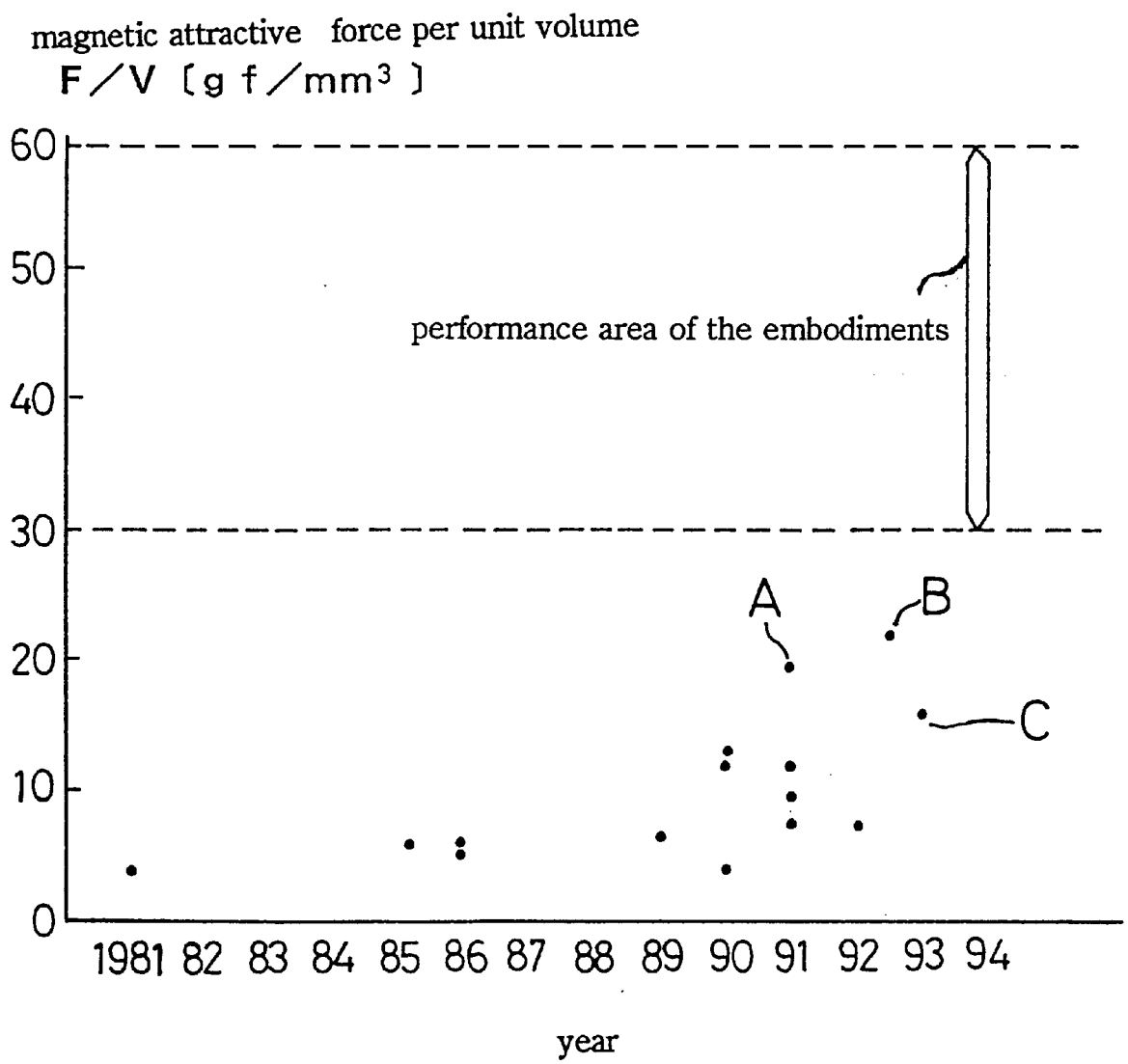
FIG. 16 is a graph showing the comparison of the performance of the dental attachments.

The attractive force per unit volume for the embodiments of the present invention are shown in FIG. 16 in comparison with the existing examples. Evidently the present invention is quite superior over existing examples.

Figure 17:
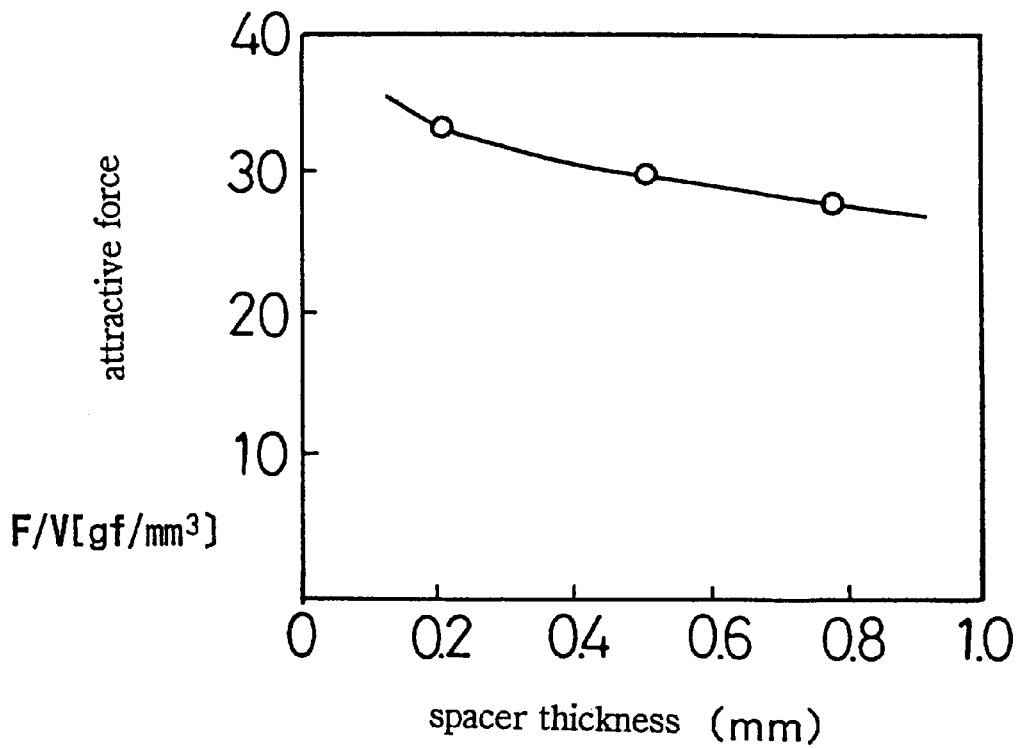
FIG. 17 is a graph showing the relation between the thickness of spacer and magnetic attractive force to the unit volume.

In the present invention spacers 21, 22 are applied to protect the magnet from corrosion and wear. The inventors have investigated the effect of the spacer thickness on the attractive force by experiment. The results are shown in FIG. 17. The thickness should be reduced to obtain strong attractive force.

Figure 18:
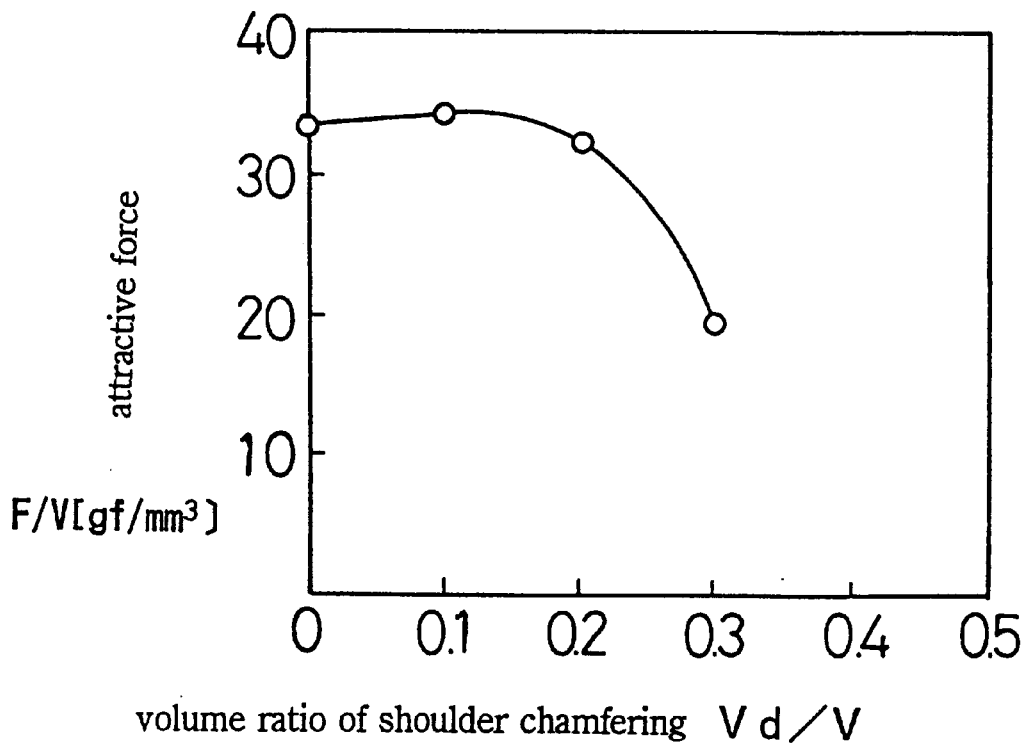
FIG. 18 is a graph showing the relation between the reduced volume at the shoulder part of the side yoke and magnetic attractive force to the unit volume.

Also an experiment is carried out to investigate the effect of chamfering at the shoulder of the side yokes 11, 12 on attractive force. As shown in FIG. 18, it is found out that the best result is obtained by a chamfered volume ratio of 0.1. The attractive force per unit volume increases at the beginning of chamfering. It may be due to the smoother flow of magnetic flux.

The invented attachment offers strong attractive force in the sever limit of volume, especially in the limit of the total height together with keeper, by applying new structure of multiple magnetic circuits.

It is shown in numerically by comparison with existing example 1 (A) and the embodiment 8 that the height of the attachment is reduced from 2.5 mm to 1.5 mm, the thickness of the keeper is reduced from 1.0 mm to 0.8 mm, and the total height of the attachment and the keeper is reduced from 3.5 mm to 2.3 mm, less than ⅔. Furthermore, the cross sectional area is reduced from 12.0 mm² to 11.0 mm², and the attractive force is increased by double, from 605 g to 1017 g. For the attractive force per unit volume the performance is improved by three times. Thus it is shown that the present invention is far more superior to the former method.

TABLE 1

Embodiment 1

| Part | dimension (mm) | | | magnetic property | | material |
|---|---|---|---|---|---|---|
| magnetic attachment (omit keeper) | height H 1.5 $H/S^{1/2} = 0.45$ | cross sectional area S 11.0 (mm²) | | | | |
| the first magnet the second magnet | height 1.2 | width 3.0 | thickness 0.45 | maximum energy product 30 MGOe | | rare earth magnet Sm2Co17 |
| central yoke | height 1.4 | width 3.0 | thickness 1.1 | saturation induction 16000 G | permeability 4000 | soft magnetic alloy 19Cr—2Mo steel |
| first side yoke second side yoke | height 1.4 | width 3.0 | thickness 0.7 | saturation induction 16000 G | permeability 4000 | soft magnetic alloy 19Cr—2Mo steel |
| spacer | height 0.2 | width 3.0 | thickness 0.45 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.8 | | | saturation induction 16000 G | permeability 4000 | soft magnetic alloy 19Cr—2Mo steel |

TABLE 2

Embodiment 2

| Part | dimension (mm) | | | magnetic property | | material |
|---|---|---|---|---|---|---|
| magnetic attachment (omit keeper) | height H 1.5 $H/S^{1/2} = 0.42$ | cross sectional area S 12.8 (mm²) | | | | |
| the first magnet the second magnet | height 1.2 | width 3.0 | thickness 0.3 | maximum energy product 30 MGOe | | rare earth magnet Sm2Co17 |
| central yoke | height 1.4 | width 3.0 | thickness 1.5 | saturation induction 16000 G | permeability 4000 | soft magnetic alloy 19Cr—2Mo steel |
| first side yoke second side yoke | height 1.4 | width 3.0 | thickness 0.95 | saturation induction 16000 G | permeability 4000 | soft magnetic alloy 19Cr—2Mo steel |
| spacer | height 0.2 | width 3.0 | thickness 0.30 | pemieability 1.02 | | non-magnetic alloy 17Cr—12Cr—2Mo steel |
| cap | thickness of cap 9.1 | | | permeability 1.02 | | non-magnetic alloy 17Cr—12Cr—2Mo steel |
| keeper | thickness 0.9 | | | saturation induction 16000 G | permeability 4000 | soft magnetic alloy 19Cr—2Mo steel |

TABLE 3

Embodiment 3

| Part | dimension (mm) | | | magnetic property | | material |
|---|---|---|---|---|---|---|
| magnetic attachment (omit keeper) | height H 1.3 $H/S^{1/2} = 0.37$ | cross sectional area S 12.4 (mm²) | | | | |
| the first magnet the second magnet | height 1.2 | width 3.0 | thickness 0.65 | maximum energy product 30 MGOe | | rare earth magnet Sm2Co17 |
| central yoke | height 1.2 | width 3.0 | thickness 1.2 | saturation induction 16000 G | permeability 4000 | soft magnetic alloy 19Cr—2Mo steel |
| first side yoke second side yoke | height 1.2 | width 3.0 | thickness 0.75 | saturation induction 16000 G | permeability 4000 | soft magnetic alloy 19Cr—2Mo steel |
| spacer | height 0.2 | width 3.0 | thickness 0.65 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.75 | | | saturation induction 16000 G | permeability 4000 | soft magnetic alloy 19Cr—2Mo steel |

TABLE 4

Embodiment 4

| Part | dimension (mm) | | | magnetic property | | material |
|---|---|---|---|---|---|---|
| magnetic attachment (omit keeper) | height H 1.6 $H/S^{1/2} = 0.51$ | cross sectional area S 9.8 (mm$^2$) | | | | |
| the first magnet the second magnet | height 1.2 | width 3.0 | thickness 0.45 | maximum energy product 30 MGOe | | rare earth magnet Sm2Co17 |
| central yoke | height 1.6 | width 3.0 | thickness 1.1 | saturation induction 16000 G | permeability 4000 | soft magnetic alloy 19Cr—2Mo steel |
| first side yoke second side yoke | height 1.6 | width 3.0 | thickness 0.7 | saturation induction 16000 G | permeability 4000 | soft magnetic alloy 19Cr—2Mo steel |
| case | thickness of case 0.2 | width 3.0 | | permeability 1.02 | | non-magnetic alloy 17Cr—12Cr—2Mo steel |
| keeper | thickness 0.7 | | | saturation induction 16000 G | permeability 4000 | soft magnetic alloy 19Cr—2Mo steel |

TABLE 5

Embodiment 5

| Part | dimension (mm) | | | magnetic property | | material |
|---|---|---|---|---|---|---|
| magnetic attachment (omit keeper) | height H 1.5 $H/S^{1/2} = 0.45$ | cross sectional area S 11.0 (mm$^2$) | | | | |
| the first magnet the second magnet | height 1.2 | width 3.0 | thickness 0.45 | maximum energy product 30 MGOe | | rare earth magnet Sm2Co17 |
| central yoke | height 1.4 | width 3.0 | thickness 1.1 | saturation induction 16000 G | permeability 4000 | soft magnetic alloy 19Cr—2Mo steel |
| first side yoke second side yoke | height 1.4 chamfered shoulder (FIG. 5) | width 3.0 | thickness 0.7 | saturation induction 16000 G | permeability 4000 | soft magnetic alloy 19Cr—2Mo steel |
| spacer | height 0.2 | width 3.0 | thickness 0.45 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.7 | | | saturation induction 16000 G | permeability 4000 | soft magnetic alloy 19Cr—2Mo steel |

TABLE 6

Embodiment 6

| Part | dimension (mm) | | | magnetic property | | material |
|---|---|---|---|---|---|---|
| magnetic attachment (omit keeper) | height H 1.5 $H/S^{1/2} = 0.45$ | cross sectional area S 11.0 (mm$^2$) | | | | |
| the first magnet the second magnet | height 1.2 | width 3.0 | thickness 0.45 | maximum energy product 30 MGOe | | rare earth magnet Sm2Co17 |
| central yoke | height 1.4 V-shaped groove on top, bridge-like part (FIG. 6) | width 3.0 | thickness 1.1 | saturation induction 16000 G | permeability 4000 | soft magnetic alloy 19Cr—2Mo steel |
| first side yoke second side yoke | height 1.4 | width 3.0 | thickness 0.7 | saturation induction 16000 G | permeability 4000 | soft magnetic alloy 19Cr—2Mo steel |
| spacer | height 0.2 | width 3.0 | thickness 0.45 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.7 | | | saturation induction 16000 G | permeability 4000 | soft magnetic alloy 19Cr—2Mo steel |

TABLE 7

Embodiment 7

| Part | dimension (mm) | | | magnetic property | | material |
|---|---|---|---|---|---|---|
| magnetic attachment (omit keeper) | height H 1.5 $H/S^{1/2} = 0.45$ | cross sectional area S 11.0 (mm$^2$) | | | | |
| the first magnet the second magnet | height 1.2 | width 3.0 | thickness 0.45 | maximum energy product 35 MGOe | | rare earth magnet Nd14Fe77B8 |
| central yoke | height 1.4 | width 3.0 | thickness 1.1 | saturation induction 16000 G | permeability 4000 | soft magnetic alloy 19Cr—2Mo steel |
| first side yoke second side yoke | height 1.4 | width 3.0 | thickness 0.7 | saturation induction 16000 G | permeability 4000 | soft magnetic alloy 19Cr—2Mo steel |
| spacer | height 0.2 | width 3.0 | thickness 0.45 | permeability 1.02 | | non-magnetic alloy Ti |
| cap | thickness of cap 0.1 | | | permeability 1.02 | | non-magnetic alloy Ti |
| keeper | thickness 0.8 | | | saturation induction 16000 G | permeability 4000 | soft magnetic alloy 19Cr—2Mo steel |

TABLE 8

Embodiment 8

| Part | dimension (mm) | | | magnetic property | | material |
|---|---|---|---|---|---|---|
| magnetic attachment (omit keeper) | height H 1.5 $H/S^{1/2} = 0.45$ Cr diffusion layer of 20 μm thick at attracting face | cross sectional area S 11.0 (mm$^2$) | | | | |
| the first magnet the second magnet | height 1.2 | width 3.0 | thickness 0.45 | maximum energy product 30 MGOe | | rare earth magnet Sm2Co17 |
| central yoke | height 1.4 | width 3.0 | thickness 1.1 | saturation induction 24000 G | permeability 9000 | soft magnetic alloy Fe—49Co—2V |
| first side yoke second side yoke | height 1.4 | width 3.0 | thickness 0.7 | saturation induction 24000 G | permeability 9000 | soft magnetic alloy Fe—49Co—2V |
| spacer | height 0.2 | width 3.0 | thickness 0.45 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.6 | | | saturation induction 16000 G | permeability 4000 | soft magnetic alloy 19Cr—2Mo steel |

TABLE 9

Embodiment 9

| Part | dimension (mm) | | | magnetic property | | material |
|---|---|---|---|---|---|---|
| magnetic attachment (omit keeper) | height H 1.5 $H/S^{1/2} = 0.45$ Cr diffusion layer of 20 μm thick at attracting face | cross sectional area S 11.0 (mm$^2$) | | | | |
| the first magnet the second magnet | height 1.2 | width 3.0 | thickness 0.45 | maximum energy product 30 MGOe | | rare earth magnet Sm2Co17 |
| central yoke | height 1.4 | width 3.0 | thickness 1.1 | saturation induction 22000 G | permeability 10000 | soft magnetic alloy pure iron |
| first side yoke second side yoke | height 1.4 | width 3.0 | thickness 0.7 | saturation induction 22000 G | permeability 10000 | soft magnetic alloy pure iron |
| spacer | height 0.2 | width 3.0 | thickness 0.45 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.6 | | | saturation induction 22000 G | permeability 10000 | soft magnetic alloy pure iron |

TABLE 10

Embodiment 10

| Part | dimension (mm) | | | magnetic property | | material |
|---|---|---|---|---|---|---|
| magnetic attachment (omit keeper) | height H 1.03 $H/S^{1/2} = 0.31$ | cross sectional area S 11.0 (mm²) | | | | |
| the first magnet the second magnet | height 0.8 | width 3.0 | thickness 0.3 | maximum energy product 30 MGOe | | rare earth magnet Sm2Co17 |
| central yoke | height 0.93 | width 3.0 | thickness 0.78 | saturation induction 16000 G | permeability 4000 | soft magnetic alloy 19Cr—2Mo steel |
| first side yoke second side yoke | height 0.93 | width 3.0 | thickness 0.47 | saturation induction 16000 G | permeability 4000 | soft magnetic alloy 19Cr—2Mo steel |
| spacer | height 0.13 | width 3.0 | thickness 0.3 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.45 | | | saturation induction 16000 G | permeability 4000 | soft magnetic alloy 19Cr—2Mo steel |

TABLE 11

Embodiment 11

| Part | dimension (mm) | | | magnetic property | | material |
|---|---|---|---|---|---|---|
| magnetic attachment (omit keeper) | height H 1.2 $H/S^{1/2} = 0.39$ | cross sectional area S 9.6 (mm²) | | | | |
| the first magnet the second magnet | height 1.0 | width 2.6 | thickness 0.6 | maximum energy product 35 MGOe | | rare earth magnet Nd14Fe77B8 |
| central yoke | height 1.2 | width 2.8 | thickness 0.6 | saturation induction 16000 G | permeability 4000 | soft magnetic alloy 19Cr—2Mo steel |
| first side yoke second side yoke | height 1.2 | width 2.8 | thickness 0.6 | saturation induction 16000 G | permeability 4000 | soft magnetic alloy 19Cr—2Mo steel |
| annular case | thickness of case 0.1 | width 2.8 | | permeability 1.02 | | non-magnetic alloy 17Cr—12Cr—2Mo steel |
| keeper | thickness 0.6 | | | saturation induction 16000 G | permeability 4000 | soft magnetic alloy 19Cr—2Mo steel |

TABLE 12

Embodiment 12

| Part | dimension (mm) | | | magnetic property | | material |
|---|---|---|---|---|---|---|
| magnetic attachment (omit keeper) | height H 2.4 $H/S^{1/2} = 0.78$ | cross sectional area S 9.6 (mm²) | | | | |
| magnet | height 2.0 | width 2.6 | thickness 1.2 | maximum energy product 35 MGOe | | rare earth magnet Nd14Fe77B8 |
| first side yoke second side yoke | height 2.4 | width 2.8 | thickness 1.2 | saturation induction 16000 G | permeability 4000 | soft magnetic alloy 19Cr—2Mo steel |
| annular case | thickness of case 0.2 | width 2.8 | | permeability 1.02 | | non-magnetic alloy 17Cr—12Cr—2Mo steel |
| keeper | thickness 1.2 | | | saturation induction 16000 G | permeability 4000 | soft magnetic alloy 19Cr—2Mo steel |

TABLE 13

Exsisting example 1 (A)

| Part | dimension (mm) | | | magnetic property | | material |
|---|---|---|---|---|---|---|
| magnetic attachment (omit keeper) | height H 1.5 $H/S^{1/2} = 0.72$ | cross sectional area S 12.0 (mm$^2$) | | | | |
| magnet | height 2.1 | width 4.0 | thickness 1.0 | maximum energy product 30 MGOe | | rare earth magnet Sm2Co17 |
| first side yoke second side yoke | height 2.4 | width 4.0 | thickness 1.0 | saturation induction 16000 G | permeability 4000 | soft magnetic alloy 19Cr—2Mo steel |
| spacer | height 0.3 | width 4.0 | thickness 1.0 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 1.0 | | | saturation induction 16000 G | permeability 4000 | soft magnetic alloy 19Cr—2Mo steel |

TABLE 14

Exsisting example 2 (B)

| Part | dimension (mm) | | | magnetic property | | material |
|---|---|---|---|---|---|---|
| magnetic attachment (omit keeper) | height H 1.5 $H/S^{1/2} = 0.43$ | cross sectional area S 12.0 (mm$^2$) | | | | |
| magnet | height 1.1 | width 4.0 | thickness 1.0 | maximum energy product 30 MGOe | | rare earth magnet Sm2Co17 |
| first side yoke second side yoke | height 1.4 | width 4.0 | thickness 1.0 | saturation induction 16000 G | permeability 4000 | soft magnetic alloy 19Cr—2Mo steel |
| spacer | height 0.3 | width 4.0 | thickness 1.0 | permeability 1.02 | | non-magnetic alloy 17Cr—12Cr—2Mo steel |
| cap | thickness of cap 0.1 | | | permeability 1.02 | | non-magnetic alloy 17Cr—12Cr—2Mo steel |
| keeper | thickness 0.8 | | | saturation induction 16000 G | permeability 4000 | soft magnetic alloy 19Cr—2Mo steel |

TABLE 15

Exsisting example 3 (C)

| Part | dimension (mm) | | | magnetic property | | material |
|---|---|---|---|---|---|---|
| magnetic attachment (omit keeper) | height H 1.5 $H/S^{1/2} = 0.42$ | cross sectional area S 12.6 (mm$^2$) | | | | |
| magnet | height 1.0 | diameter 3.0 | | maximum energy product 20 MGOe | | rare earth magnet SmCo5 |
| cup yoke | height 1.5 | diameter 0.5 | | saturation induction 11000 G | permeability 4000 | soft magnetic alloy 30Cr—2Mo steel |
| disk yoke | height 0.2 | diameter 2.8 | | saturation induction 11000 G | permeability 4000 | non-magnetic alloy 17Cr—12Cr—2Mo steel |
| shield ring | height 0.2 | outer diameter 3.0 | inner diameter 2.6 | permeability 1.02 | | non-magnetic alloy 17Cr—13Cr—2Mo steel |
| keeper | thickness 1.0 | | | saturation induction 11000 G | permeability 4000 | soft magnetic alloy 30Cr—2Mo steel |

TABLE 16

Exsisting example 4

| Part | dimension (mm) | | | magnetic property | material |
|---|---|---|---|---|---|
| magnetic attachment (omit keeper) | height H 1.5 $H/S^{1/2} = 0.45$ | cross sectional area S 11.0 (mm$^2$) | | | |
| magnet | height 1.2 | width 3.0 | thickness 0.9 | maximum energy product 30 MGOe | rare earth magnet Sm2Co17 |

TABLE 16-continued

Exsisting example 4

| Part | dimension (mm) | | | magnetic property | | material |
|---|---|---|---|---|---|---|
| first side yoke | height | width | thickness | saturation induction | permeability | soft magnetic alloy |
| second side yoke | 1.4 | 3.0 | 0.7 | 16000 G | 4000 | 19Cr—2Mo steel |
| spacer | height | width | thickness | permeability | | non-magnetic alloy |
|  | 0.2 | 3.0 | 0.9 | 1.02 | | 17Cr—12Cr—2Mo steel |
| cap | thickness of cap | | | permeability | | non-magnetic alloy |
|  | 0.1 | | | 1.02 | | 17Cr—12Cr—2Mo steel |
| keeper | thickness | | | saturation induction | permeability | soft magnetic alloy |
|  | 0.8 | | | 16000 G | 4000 | 19Cr—2Mo steel |

TABLE 17

Dimensions and Performances for the embodiments, the comparative example, the existing examples

|  | attractive force (gf) | F/V (gf/mm³) | dental attachment height H (mm) | keeper height (mm) | total height (mm) | cross sectional area (mm²) | H/S$^{1/2}$ | TH/S$^{1/2}$ |
|---|---|---|---|---|---|---|---|---|
| Embodiment 1 | 607 | 36.9 | 1.5 | 0.8 | 2.3 | 11.0 | 0.45 | 0.69 |
| Embodiment 2 | 618 | 32.3 | 1.5 | 0.9 | 2.4 | 12.8 | 0.42 | 0.67 |
| Embodiment 3 | 564 | 35.1 | 1.3 | 0.75 | 2.05 | 12.4 | 0.37 | 0.58 |
| Embodiment 4 | 590 | 40.1 | 1.6 | 0.7 | 2.3 | 9.8 | 0.51 | 0.73 |
| Embodiment 5 | 603 | 36.5 | 1.5 | 0.7 | 2.2 | 11.0 | 0.45 | 0.66 |
| Embodiment 6 | 601 | 36.4 | 1.5 | 0.7 | 2.2 | 11.0 | 0.45 | 0.66 |
| Embodiment 7 | 666 | 40.4 | 1.5 | 0.8 | 2.3 | 11.0 | 0.45 | 0.69 |
| Embodiment 8 | 1017 | 61.6 | 1.5 | 0.6 | 2.1 | 11.0 | 0.45 | 0.63 |
| Embodiment 9 | 818 | 49.6 | 1.5 | 0.6 | 2.1 | 11.0 | 0.45 | 0.63 |
| Embodiment 10 | 515 | 53.3 | 1.03 | 0.45 | 1.48 | 11.2 | 0.31 | 0.44 |
| Embodiment 11 | 620 | 53.8 | 1.2 | 0.6 | 1.8 | 9.6 | 0.39 | 0.58 |
| Comparative Example | 620 | 26.9 | 2.4 | 1.2 | 3.6 | 9.6 | 0.78 | 1.16 |
| Exisiting example 1 | 605 | 20.2 | 2.5 | 1.0 | 3.5 | 12.0 | 0.72 | 1.01 |
| Exisiting example 2 | 400 | 22.2 | 1.5 | 0.8 | 2.3 | 12.0 | 0.43 | 0.66 |
| Exisiting example 3 | 352 | 18.6 | 1.5 | 1.0 | 2.5 | 12.6 | 0.42 | 0.7 |
| Exisiting example 4 | 335 | 20.3 | 1.5 | 0.8 | 2.3 | 11.0 | 0.45 | 0.69 |

What is claimed is:

1. A dental magnetic attachment to be embedded in a denture base so as to face a soft magnetic keeper embedded in a top of a root surface and to attract the keeper by magnetic force, said dental magnetic attachment comprising:

at least three yokes made of soft magnetic material, at least two pieces of magnet sandwiched by two of the yokes and having a magnetization direction extending parallel to a thickness and like poles of each magnet faces each other, sandwiching a central, third yoke in between, each magnet forming an independent magnetic circuit generating magnetic flux, passing through one of said yokes in contact with the magnet, said keeper, and another of said yokes, wherein, a ratio of H/S$^{1/2}$, where H denotes a height of the magnet and S denotes an area of an attracting face, is not more than 0.55 and an attractive force is not less than 500 gf.

2. A dental magnetic attachment to be embedded in a denture base so as to face a soft magnetic keeper embedded in a top of a root surface and to attract the keeper by magnetic force, said dental magnetic attachment comprising:

a central yoke made of soft magnetic material, a first magnet having a magnetization direction parallel to a direction of its thickness and being placed in contact with one face of the central yoke, a second magnet having a magnetization direction parallel to a direction of its thickness and being placed in contact with another face of the central yoke so that like poles of the first and second magnet face each other, one of two outer yokes being made of soft magnetic material and placed in contact with a face of the first magnet, opposite to a face in contact with the central yoke, the other of the two outer yokes also being made of soft magnetic material and placed in contact with a face of the second magnet, opposite to a face in contact with the central yoke, wherein, a first magnetic circuit is formed in which magnetic flux generated at the first magnet, passes through said central yoke, said keeper and said one of the outer yokes and a second magnetic circuit is formed in which magnetic flux generated at the second magnet, passes through said central yoke, said keeper and said other of the outer yokes, and a ratio of $H/S^{1/2}$, wherein H denotes a height of the magnet and S denotes an area of an attracting face, is not more than 0.55 and an attractive force is not less than 500 gf.

3. A dental magnetic attachment as set forth in claim 2, wherein, a surface of the attachment is covered by a corrosion-resistant case.

4. A dental magnetic attachment as set forth in claim 2, wherein, a surface of the magnets that is not in contact with said central yoke and said outer yokes is covered by a corrosion-resistant case.

5. A dental magnetic attachment as set forth in claim 4, wherein, said case that is in contact with said central yoke and said outer yokes is welded to said central yoke and said outer yoke.

6. A dental magnetic attachment as set forth in claim 2, wherein the central yoke, the magnets, and the outer yokes are covered by a cap made of corrosion resistant non-magnetic material and an attracting face for attachment to the keeper, and an attracting face of the magnets are covered by spacers made of corrosion resistant non-magnetic material.

7. A dental magnetic attachment as set forth in claim 6, wherein, one side of the central yoke has a V-shaped groove and said cap has a similar shape to said yoke, and a bridge is placed on the V-shaped groove.

8. A dental magnetic attachment as set forth in claim 6, wherein, said central yoke and said outer yokes are made of corrosion-resistant soft-magnetic material with a saturation magnetization of not less than 20000 G, and at least one of said spacer and said case is made of non-magnetic material with a permeability of not more than 1.2.

9. A dental magnetic attachment as set forth in claim 2, wherein, lateral faces of said magnets are covered with a corrosion resistant non-magnetic annular case.

10. A dental magnetic attachment as set forth in claim 2, wherein, a rare earth magnet with a maximum energy product of not less than 20 MGOe is used for the magnets.

11. A dental magnetic attachment as set forth in claim 2, wherein, said central yoke and said outer yokes are made of corrosion resistant soft magnetic material with a saturation magnetization of not less than 20000 G, and the outer yokes are covered by a corrosion-resistant case.

12. A dental magnetic attachment as set forth in claim 2, wherein, a shoulder part of the outer yokes are chamfered.

13. A dental magnetic attachment as set forth in claim 2, wherein, a shape of a cross section parallel to an attracting face is one of a polygon, an eclipse, and a pseudo-circle.

14. A dental magnetic attachment as set forth in claim 2, wherein, the one side of the central yoke has a V-shaped groove in a center.

15. A dental magnetic attachment as set forth in claim 2, wherein, the outer yokes have a groove on an outer side as an anchor for the fixation of attachment to the denture.

16. A dental magnetic attachment as set forth in claim 2, wherein, an area of an attracting face is not more than 20.0 mm².

17. A dental magnetic attachment to be embedded in a denture base so as to face a soft magnetic keeper embedded in a top of a root surface and to attract the keeper by magnetic force, said dental magnetic attachment comprising:

two central yokes having a face extending parallel to a direction of thickness being a magnetic attracting face to the keeper, a central magnet having a magnetization direction parallel to a direction of a thickness and being sandwiched by two central yokes, a first magnet having a magnetization direction parallel to a direction of a thickness and which is placed in contact with a face of one central yoke so that a like pole of the first magnet and the central magnet faces each other, one of two outer yokes being placed in contact with a face of the first magnet, on an opposite face to a face in contact with one of the central yokes, a second magnet having a magnetization direction parallel to a direction of a thickness and which is placed in contact with the other of the central yokes so that like poles of the second magnet and the central magnet face each other, and the other of the two outer yokes also being placed in contact with a face of the second magnet, which is an opposite face to the one face in contact with one of the central yokes, wherein, a first magnetic circuit is formed in which magnetic flux generated at the first magnet, passes through one of said central yoke, said keeper and one of said outer yokes, and a second magnetic circuit is formed in which magnetic flux generated at the central magnet, passes through one of said central yokes, said keeper, and the other of said central yokes, and a third magnetic circuit is formed in which magnetic flux generated at the second magnet, passes through the other of said central yokes, said keeper and the other of said outer yokes, and a ratio of $H/S^{1/2}$, where H denotes a height of the magnet and S denotes an area of an attracting face, is not more than 0.55 and an attractive force is not less than 500 gf.

18. A dental magnetic attachment as set forth in claim 17, wherein, a surface of the first, second and the third magnet is covered by a corrosion-resistant case.

19. A dental magnetic attachment as set forth in claim 18, wherein, said case that is in contact with said central yoke, said one outer yoke, and said other outer yoke is welded to them.

20. A dental magnetic attachment as set forth in claim 17, wherein, the outer yokes have a groove on each outer side as an anchor for a fixation of attachment to the denture.

21. A dental magnetic attachment as set forth in claim 17, wherein, the area of the attracting face is not more than 20.0 mm².

22. A dental magnetic attachment to be embedded in a denture base so as to face a soft magnetic keeper embedded in a top of a root surface and to attract the keeper by magnetic force, said dental magnetic attachment comprising:

at least three yokes made of soft magnetic material with one face extending parallel to a direction of thickness and forming magnetic attracting faces to said keeper, and at least two pieces of magnet sandwiched by the yokes and having a magnetization direction parallel to a thickness and like poles of each magnet faces each other sandwiching a yoke in between and having a corrosion-resistant coating on the faces, and each magnet forms a mutually independent magnetic circuit in which magnetic flux generated at the magnet, passes through one of said yokes holding the magnet, said keeper, and the other of said yokes.

23. A dental magnetic attachment as set forth in claim 22, wherein, a case is welded with a central yoke and a outer yokes.

24. A dental magnetic attachment as set forth in claim 22, wherein, two outer yokes have a groove on each outer side as an anchor for a fixation of attachment to the denture.

25. A dental magnetic attachment as set forth in claim 22 wherein, an area of an attracting face is not more than 20.0 mm$^2$.

26. A dental magnetic attachment embedded in a denture base to be magnetically attached to a soft magnetic keeper embedded in a top of a root surface said dental magnetic attachment comprising:

- at least three yokes made of corrosion resistant soft magnetic material, spaced from each other, to be magnetically attached to said soft magnetic keeper,
- at least two magnets each of which is sandwiched by two of said yokes and having their magnetic poles facing said yokes and each two of said poles facing each other through one of said yokes being a same pole, and
- magnet covers made of corrosion resistant non-magnetic material covering a lateral surface of each of said magnets and welded to two of said yokes to cover an entire surface of each of said magnets with said magnet covers and said yokes.

27. A dental magnetic attachment as set forth in claim 26, wherein a ratio of $H/S^{1/2}$, in which H denotes a height of a magnet and S denotes an area of an attracting face, is not more than 0.55 and an attractive force is not less than 500 gf.

28. A dental magnetic attachment as set forth in claim 27, wherein, the area of the attracting face is not more than 20.0 mm$^2$.

29. A dental magnetic attachment as set forth in claim 26, wherein a number of said yokes is three and a number of said magnets is two.

30. A dental magnetic attachment as set forth in claim 26, wherein a number of said yokes is four and a number of said magnets is three.

31. A dental magnetic attachment as set forth in claim 26, wherein, the farther side of each of said yokes, sandwiched with two of said magnets, to the keeper has a V-shaped groove and a bridge is placed on the V-shaped groove.

32. A dental magnetic attachment as set forth in claim 26, wherein, each of said magnets is a rare earth magnet with a maximum energy product of not less than 20 MGOe.

33. A dental magnetic attachment as set forth in claim 26, wherein, a saturation magnetization of said yokes is not less than 20000 G, and a permeability of said magnet covers is not more than 1.2.

34. A dental magnetic attachment as set forth in claim 26, wherein, a shoulder part of the outer yokes among said yokes are chamfered.

35. A dental magnetic attachment as set forth in claim 26, wherein a shape of a cross section parallel to the attracting face is one of a polygon, an eclipse, and a pseudo-circle.

36. A dental magnetic attachment as set forth in claim 26, wherein, the outer yokes among said yokes have a groove on their outer sides as an anchor for a fixation of attachment to said denture.

\* \* \* \* \*